United States Patent [19]

Matsumoto et al.

[11] Patent Number: 4,666,809
[45] Date of Patent: May 19, 1987

[54] ELECTROPHOTOGRAPHIC PHOTOSENSITIVE MEMBER

[75] Inventors: Masakazu Matsumoto, Yokohama; Masataka Yamashita, Kiyose, both of Japan

[73] Assignee: Canon Kabushiki Kaisha, Tokyo, Japan

[21] Appl. No.: 750,988

[22] Filed: Jul. 1, 1985

Related U.S. Application Data

[63] Continuation of Ser. No. 521,529, Aug. 9, 1983, abandoned.

[30] Foreign Application Priority Data

Aug. 12, 1982 [JP] Japan .................. 57-139195
Aug. 26, 1982 [JP] Japan .................. 57-146945

[51] Int. Cl.$^4$ ............................. G03G 5/06
[52] U.S. Cl. ...................... 430/76; 430/59; 430/70; 430/73; 430/74; 564/251
[58] Field of Search .......... 430/59, 70, 73, 74, 430/76; 564/251

[56] References Cited

U.S. PATENT DOCUMENTS 4,278,747 7/1981 Murayama et al. .......... 430/70 X

*Primary Examiner*—John E. Kittle
*Assistant Examiner*—Mukund J. Shah
*Attorney, Agent, or Firm*—Fitzpatrick, Cella, Harper & Scinto

[57] ABSTRACT

An electrophotographic photosensitive member having a conductive substrate and a photosensitive layer, which is characterized in that the photosensitive layer comprises a binder and at least one hydrazone compound represented by the following general formula (1) or (2):

General formula (1)

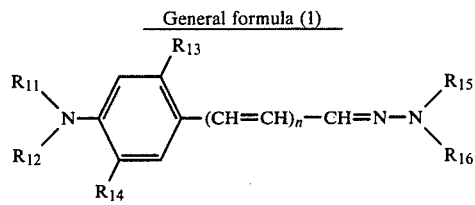

In the formula; $R_{11}$ and $R_{12}$ independently of each other represent alkyl, aralkyl, or phenyl, each substituted or unsubstituted, or $R_{11}$ and $R_{12}$ form a 5- or 6-membered ring residue conjointly with the nitrogen atom to which they are bonded; $R_{13}$ and $R_{14}$ independently of each other represent alkyl or alkoxy; $R_{15}$ and $R_{16}$ independently of each other represent alkyl, aralkyl, or aryl, wherein the aralkyl and the aryl are substituted or unsubstituted; and n represents a integer of 0 or 1.

General formula (2)

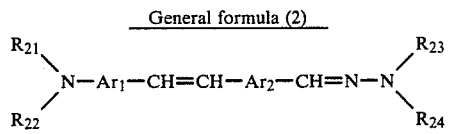

In the formula; $R_{21}$ and $R_{22}$ independently of each other represent alkyl, aralkyl, or phenyl, each substituted or unsubstituted, or $R_{21}$ and $R_{22}$ form a 5- or 6-membered ring residue conjointly with the nitrogen atom to which they are bonded; $R_{23}$ and $R_{24}$ independently of each other represent alkyl, aralkyl, or aryl, each substituted or unsubstituted; and $Ar_1$ and $Ar_2$ independently of each other represent substituted or unsubstituted arylene.

44 Claims, No Drawings

ELECTROPHOTOGRAPHIC PHOTOSENSITIVE MEMBER

This application is a continuation of application Ser. No. 521,529 filed Aug. 9, 1983, now abandoned.

BACKGROUND OF THE INVENTION

1. Field of the Invention

This invention relates to electrophotographic photosensitive members and more particularly to an electrophotographic photosensitive member containing a low molecular organic photoconductor, therewith being improved in electrophotographic characteristics.

2. Description of the Prior Art

Inorganic photoconductive materials such as selenium, cadmium sulfide, and zinc oxide have so far been known as photoconductors for use in electrophotographic photosensitive members. While having a number of advantages, for instance, chargeability to a suitable potential in the dark, little dissipation of the charge in the dark, and rapid dissipation of the charge on light exposure, these photoconductive materials suffer from various disadvantages as follows: Selenium type photosensitive members readily crystallize under the influence of environmental factors such as temperature, humidity, dust, and pressure; in particular when the ambient temperature exceeds 40° C., the crystallization becomes remarkable, thereby the chargeability being deteriorated and white spots appearing on resulting images. Cadmium sulfide type photosensitive members cannot maintain constant sensitivity under high humidity conditions. Zinc oxide type photosensitive members, which require to be sensitized with coloring matter such as Rose Bengale, a typical sensitizing colorant for this purpose, cannot give constant image quality over a long period of time because the coloring matter will undergo a charge deterioration due to repeated corona charging and will be faded by repeated light exposure.

On the other hand, a variety of organic photoconductive polymers including polyvinylcarbazole have been proposed until now. In spite of the superiority of these polymers to the above inorganic photoconductive materials in film forming property and in lightweight character, the polymers have been scarecely put to practical use because they are still unsatisfactory in film forming property and inferior to the inorganic photoconductive materials in sensitivity, durability, and stability to changes in environmental conditions.

Low-molecular organic photoconductors also have been proposed including hydrazone compounds as disclosed in U.S. Pat. No. 4,150,987 and others, triarylpyrazoline compounds as in U.S. Pat. No. 3,837,851 and others, and 9-styrylanthracene compounds as in Japanese Patent Laid-open Nos. 94828/1976 and 94829/1976. Although combined use of a suitably selected binder with these low molecular organic photoconductors has overcome the deficiency of film forming property which has been a problem in the art of organic photoconductive polymers, the low molecular organic photoconductors are rather unsatisfactory with respect to sensitivity.

In view of the above, a lamination type of photosensitive member has been proposed which has two photosensitive layers functioning separately as a charge generation layer and a charge transport layer. This type of photosensitive member can be improved in sensitivity to visible rays, retention of charge, and surface strength.

These photosensitive members are described in U.S. Pat. Nos. 3,837,851, cited above, and 3,871,882.

However, these photosensitive members employing the conventional low molecular organic photoconductor in the charge transport layer still require improvements in that sufficient sensitivity has not yet been obtained and the light area and dark area potentials vary to large extents when the photosensitive members are repeatedly charged and exposed many times.

SUMMARY OF THE INVENTION

An object of this invention is to provide an electrophotographic photosensitive member free of the above noted drawbacks or disadvantages.

Another object of this invention is to provide a novel organic photoconductor.

Still another object of this invention is to provide a novel charge-transporting material for use in the laminate type of photosensitive member having a charge generation layer and a charge transport layer.

According to one aspect of the present invention, there is provided an electrophotographic photosensitive member having a conductive substrate and a photosensitive layer, characterized in that the photosensitive layer comprises a binder and at least one hydrazone compound represented by the following formula (1) or (2):

General formula (1)

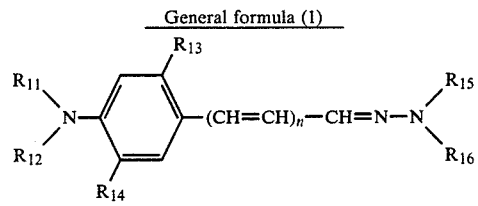

In the formula; $R_{11}$ and $R_{12}$ independently of each other represent alkyl, aralkyl, or aryl, each substituted or unsubstitued, or $R_{11}$ and $R_{12}$ from a 5- or 6-membered ring residue conjointly with the nitrogen atom to which they are bonded; $R_{13}$ and $R_{14}$ independently of each other represent alkyl or alkoxy; $R_{15}$ and $R_{16}$ independently of each other represent alkyl, aralkyl, or aryl, wherein the aralkyl and the aryl may be substituted or unsubstituted; and n represents an integer of 0 or 1.

General formula (2)

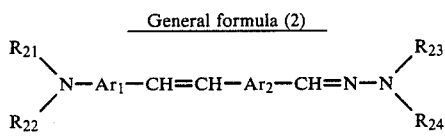

In the formula; $R_{21}$ and $R_{22}$ independently of each other represent alkyl, aralkyl, or phenyl, each substituted or unsubstituted, or $R_{21}$ and $R_{22}$ form a 5- or 6-membered ring residue conjointly with the nitrogen atom to which they are bonded; $R_{23}$ and $R_{24}$ independently of each other represent alkyl, aralkyl, or aryl, each substituted or unsubstituted; and $Ar_1$ and $Ar_2$ independently of each other represent substituted or unsubstituted arylene.

According to another aspect of the present invention, there is provided an electrophotographic photosensitive member having a conductive substrate, a charge generation layer, and a charge transport layer, characterized in that the charge transport layer comprises a binder and at least one hydrazone compound represented by the general formula (1) or (2) above.

According to further aspect of the present invention, there is provided an electrophotographic photosensitive member having a conductive substrate and a photosensitive layer, characterized in that the photosensitive layer comprises a binder, a charge-generating material, and at least one hydrazone compound represented by the general formula (1) or (2) above.

DESCRIPTION OF THE PREFERRED EMBODIMENTS

The electrophotographic photosensitive member of this invention is characterized by having at least one hydrazone compound represented by the general formula (1) or (2).

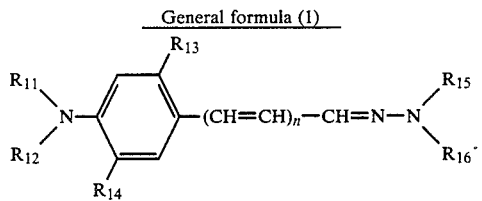

General formula (1)

In the formula; $R_{11}$ and $R_{12}$ each represent alkyl such as methyl, ethyl, propyl, or butyl; aralkyl such as benzyl, phenethyl, or naphthylmethyl; or phenyl. The alkyl can be substituted by alkoxy such as methoxy, ethoxy, propoxy, or butoxy; halogen such as fluorine, chlorine, bromine, or iodine; or dialkylamino such as dimethylamino, diethylamino, dipropylamino, or dibutylamino. The aralkyl and the phenyl can be substituted by alkyl such as methyl, ethyl, propyl, or butyl; alkoxy such as methoxy, ethoxy, propoxy, or butoxy; halogen such as fluorine, chlorine, bromine or iodine; or dialkylamino such as dimethylamino, diethylamino, dipropylamino, or dibutylamino. Alternately, $R_{11}$ and $R_{12}$ form, conjointly with the nitrogen atom to which they are bonded, a 5- or 6-membered ring residue such as pyrrolidino, piperidino, or morpholino. $R_{13}$ and $R_{14}$ each represent alkyl such as methyl, ethyl, propyl, or butyl or alkoxy such as methoxy, ethoxy, propoxy, or butoxy.

$R_{15}$ and $R_{16}$ each represent alkyl such as methyl, ethyl, propyl, or butyl; aralkyl such as benzyl, phenethyl, or naphthylmethyl; or aryl such as phenyl, naphthyl, or anthryl; wherein the aralkyl and the aryl can be substituted by the same radical as the aralkyl and the aryl for $R_{11}$ and $R_{12}$; and n is an integer of 0 or 1.

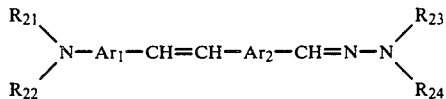

General formula (2)

In the formula; $R_{21}$ and $R_{22}$ each represent alkyl such as methyl, ethyl, propyl, or butyl; aralkyl such as benzyl, phenethyl, or naphthylmethyl; or phenyl. The alkyl can be substituted by alkoxy such as methoxy, ethoxy, propoxy, or butoxy; halogen such as fluorine, chlorine, bromine, or iodine, or dialkylamino such as dimethylamino, diethylamino, dipropylamino, or dibutylamino. The aralkyl and the phenyl can be substituted by alkyl such as methyl, ethyl, propyl, or butyl; alkoxy such as methoxy, ethoxy, propoxy, or butoxy; halogen such as fluorine, chlorine, bromine, or iodine; or dialkylamino such as dimethylamino, diethylamino, dipropylamino, or dibutylamino. Alternately $R_{21}$ and $R_{22}$ amy form conjointly with the nitrogen atom to which they are bonded, a 5- or 6-membered ring residue such as pyrrolidinyl, piperidyl, or morpholino. $R_{23}$ and $R_{24}$ each represent alkyl such as methyl, ethyl, propyl, or butyl; aralkyl such as benzyl, phenetyl, or naphthylmethyl; or aryl such as phenyl, naphthyl, or anthryl; wherein the alkyl, aralkyl, and aryl can be substituted by the same radical as the aralkyl and the aryl for $R_{21}$ and $R_{22}$. $Ar_1$ and $Ar_2$ each represent arylene such as phenylene naphthylene, or anthrylene, wherein the arylene can be substituted by alkyl such as methyl, ethyl, propyl, or butyl; alkoxy such as methoxy, ethoxy, propoxy, or butoxy; or halogen such as fluorine, chlorine, bromine, or iodine.

Typical examples of the hydrazone compounds represented by the general formula (1) or (2) are listed below.

Hydrazones represented by the general formula (1)

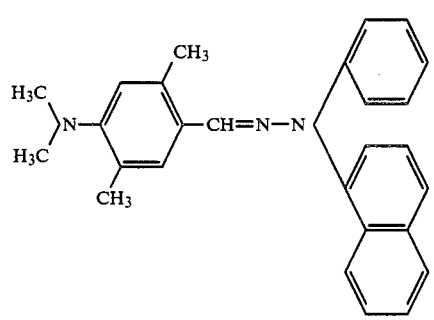

H-(1)

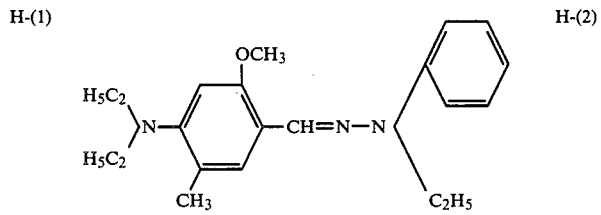

H-(2)

-continued
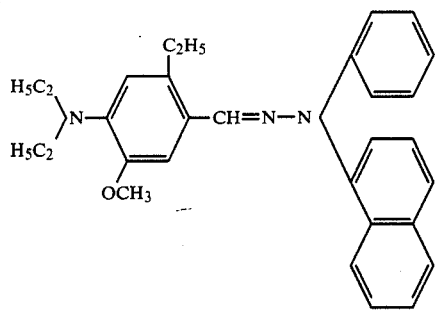
H-(3)
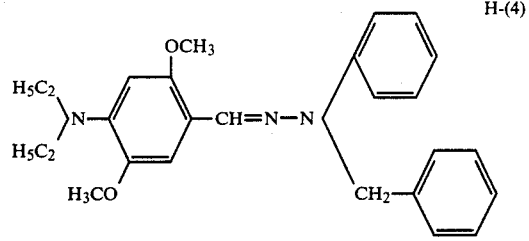
H-(4)
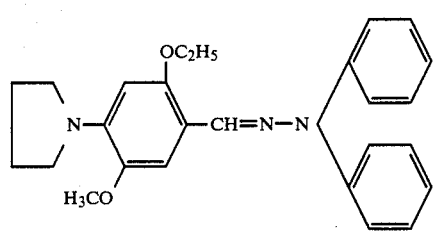
H-(5)
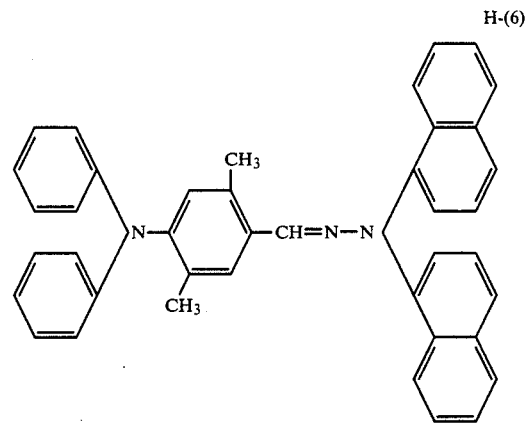
H-(6)
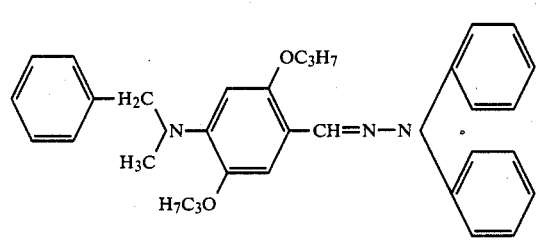
H-(7)
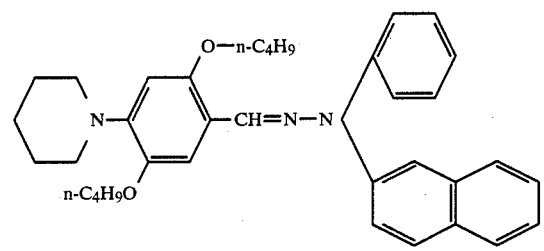
H-(8)
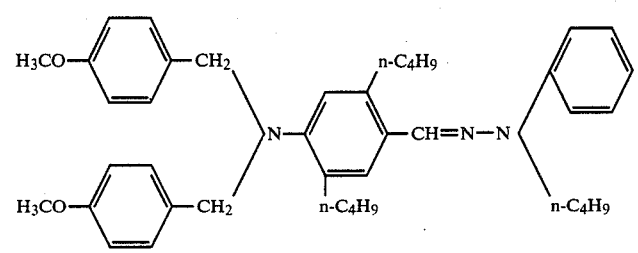
H-(9)
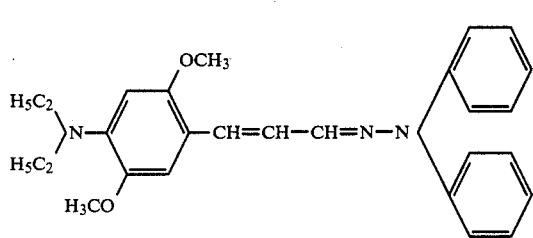
H-(10)
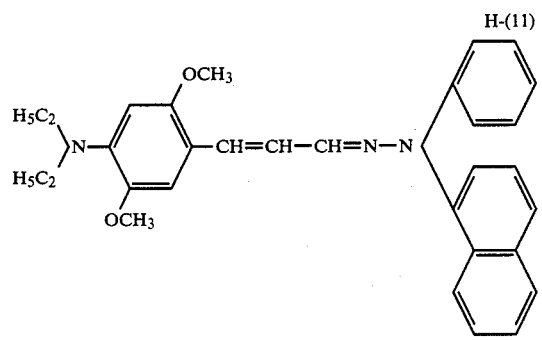
H-(11)

-continued
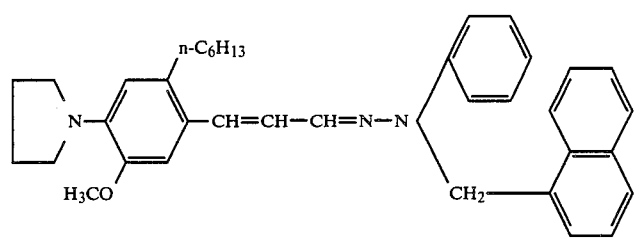
H-(12)
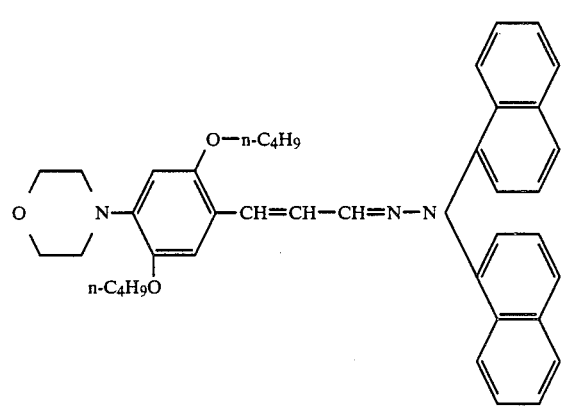
H-(13)
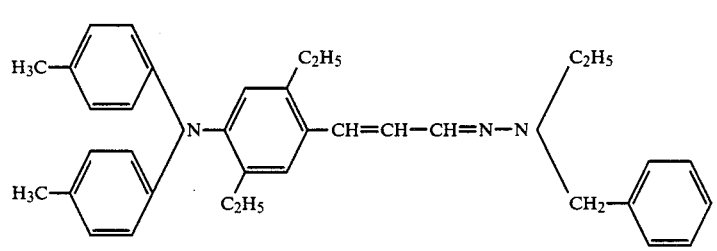
H-(14)
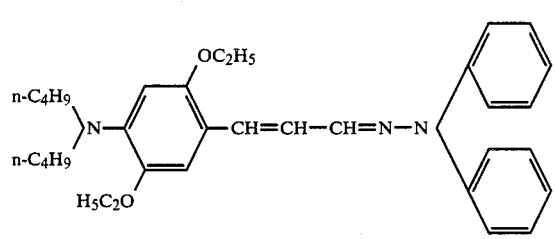
H-(15)
Hydrazones represented by the general formula (2)
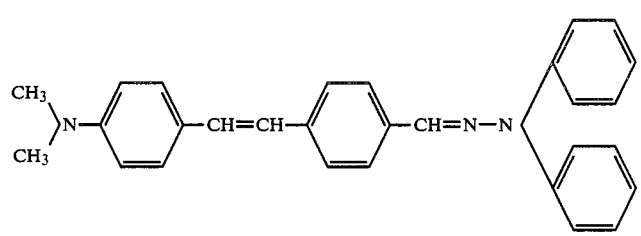
H-(16)

-continued
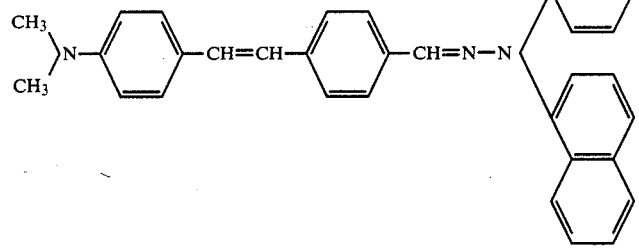
H-(17)
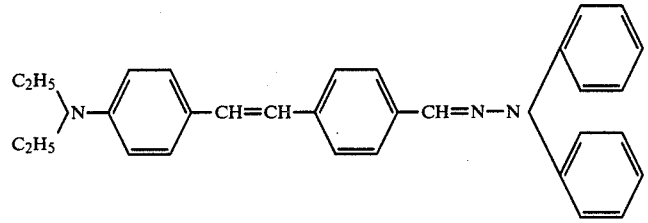
H-(18)
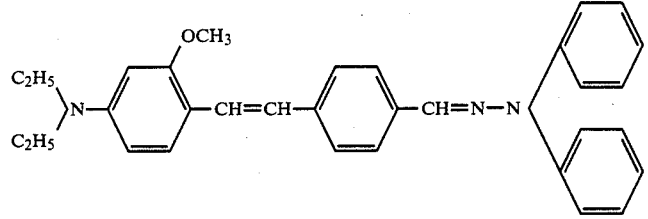
H-(19)
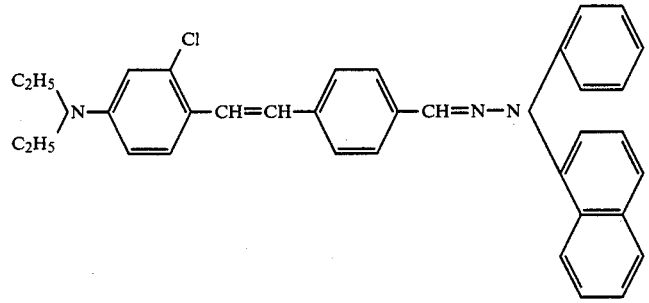
H-(20)
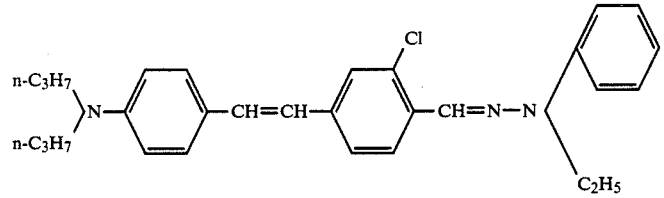
H-(21)
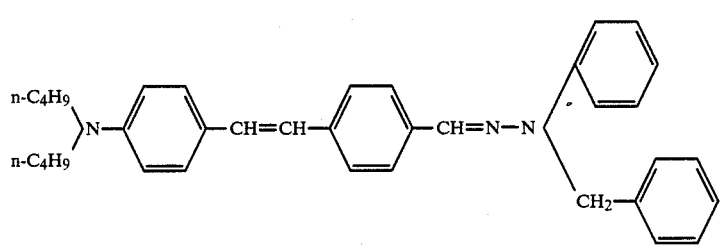
H-(22)

-continued
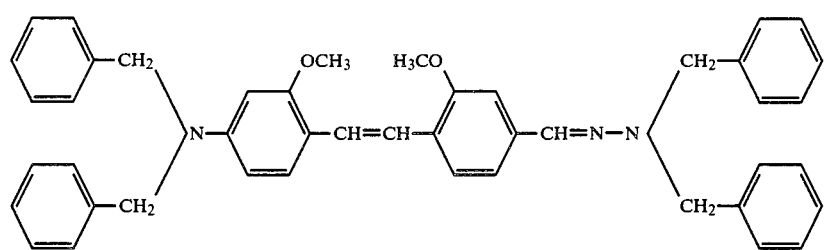
H-(23)
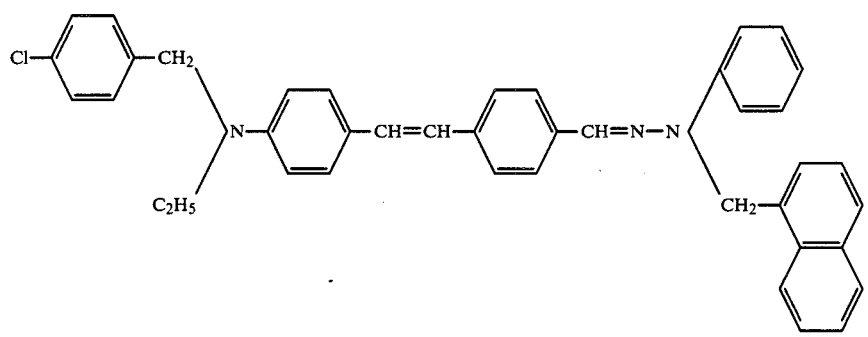
H-(24)
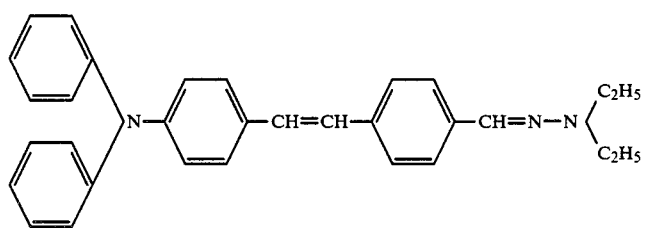
H-(25)
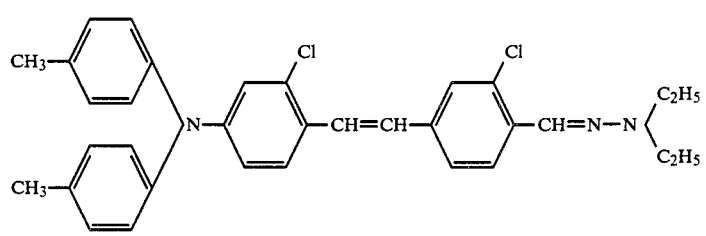
H-(26)
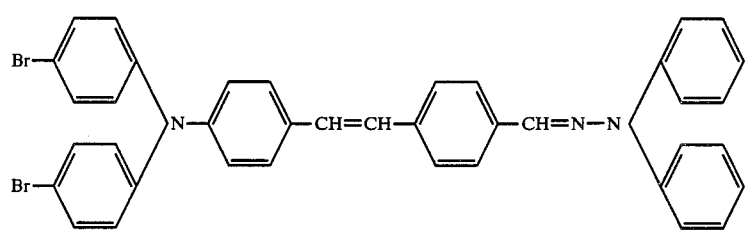
H-(27)
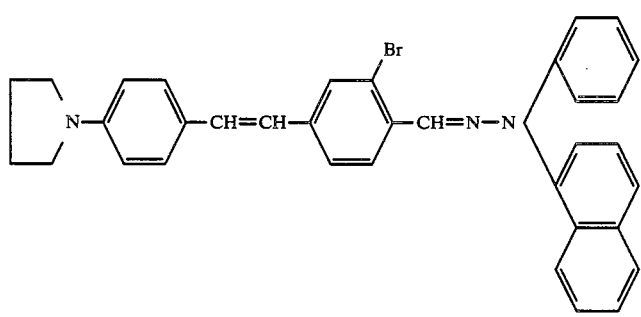
H-(28)

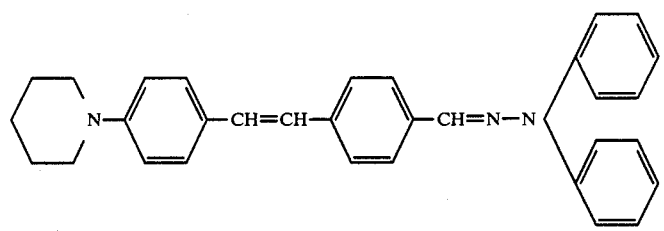
H-(29)
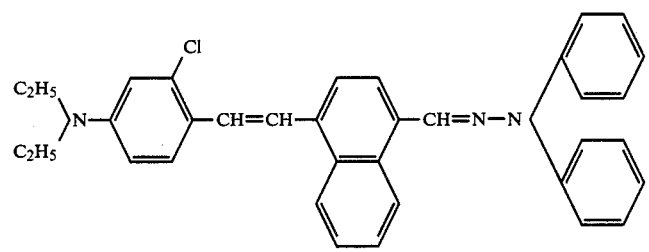
H-(30)
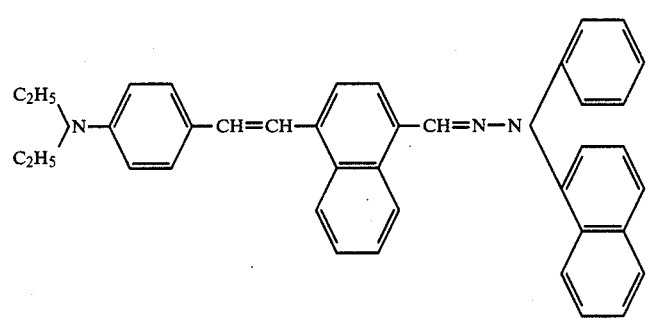
H-(31)
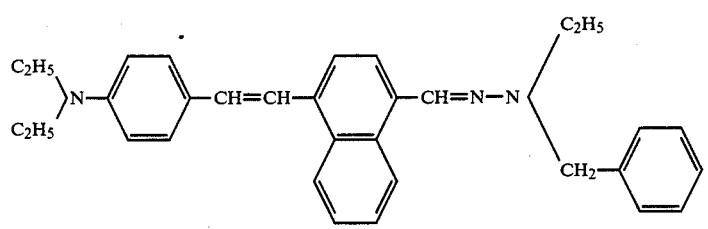
H-(32)
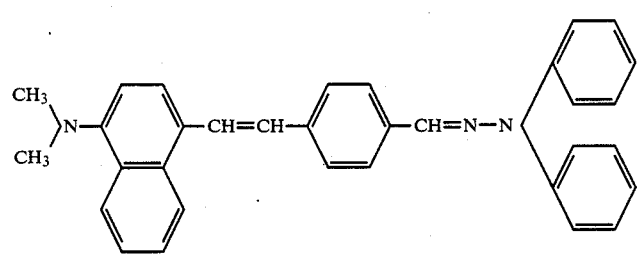
H-(33)
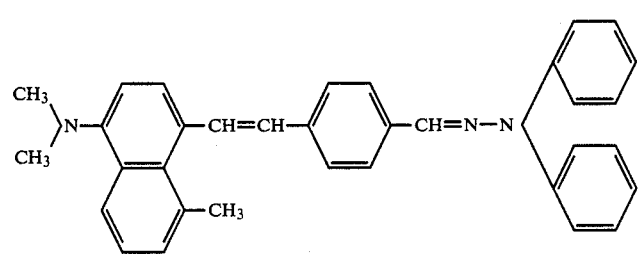
H-(34)

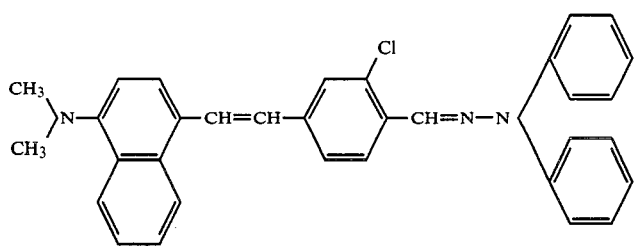

H-(35)

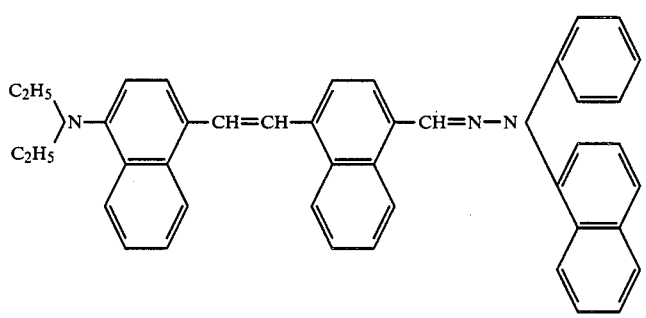

H-(36)

Further, typical examples of the process for preparing the present hydrazone compound are given below.

PREPARATION EXAMPLE 1

Synthesis of compound H-(1)

51.8 g (0.236 mole) of N-phenyl-α-naphthylamine was dissolved in a mixture of 240 ml of ethanol and 240 ml of acetic acid. 17.9 g (0.26 mole) of sodium nitrite was added to the solution with stirring at room temperature over a period of 20 minutes. Successively, 33.6 g (0.59 mole) of zinc dust was added for 20 minutes while controlling the liquid temperature at 20°–35° C. After the addition of zinc dust, stirring of the reaction mixture was continued for further 40 minutes. The formed precipitate and the unreacted zinc dust were removed by filtration. A solution of 37.6 g (0.212 mole) of 4-dimethylamino-2,5-dimethylbenzaldehyde in 45 ml of methanol was added to the filtrate with stirring at a room temperature. The resulting large amount of yellow precipitate was filtered off, dried, and recrystallized from a mixed solvent of 100 ml of methanol and 150 ml of methyl ethyl ketone, giving 37.5 g of yellow crystals of the intended hydrazone compound, yield 45%, m.p. 157°–158° C.

Analysis, Calcd (%) for $C_{27}H_{27}N_3$: C 82.4, H 6.92, N 10.68; Found (%): C 82.5, H 6.85, N 10.77.

PREPARATION EXAMPLE 2

Synthesis of compound H-(17)

64.7 g (0.275 mole) of N-phenyl-α-naphthylamine was dispersed in a mixture of 350 ml of ethanol and 350 ml of acetic acid. 22.4 g (0.325 mole) of sodium nitrite was added to the dispersion with stirring at a room temperature in 20 minutes. Successively 67.5 g (1.03 moles) of zinc dust was added in 30 minutes while controlling the liquid temperature at 20°–35° C. After the addition of zinc dust, stirring of the reaction mixture was continued for further 40 minutes. The unreacted zinc dust and formed crystals were removed by filtration. A solution of 74.3 g (0.266 mole) of 4-(4'-diethylaminostyryl)benzaldehyde in 100 ml of ethanol was added dropwise to the filtrate with stirring at a room temperature. The resulting large amount of yellow powdery precipitate was filtered and recrystallized from a mixed solvent of 150 ml of methanol and 280 ml of methyl ethyl ketone, giving 56.6 g of pale yellow crystals of the intended hydrazone compound. Yield=42.9%, m.p. 173.4°–174.2° C.

Analysis: Calcd (%) for $C_{35}H_{33}N_3$: C 84.8, H 6.71, N 8.48; Found (%): C 84.67, H 6.68, N 8.52.

Other hydrazone compounds of this invention can be synthesized with ease by the condensation reaction of an amine and a benzaldehyde derivative in a similar way as described in the above Preparation Examples.

In preferred embodiments of this invention, the hydrazone compound represented by the general formula (1) or (2) is used as a charge-transporting material for the electrophotographic photosensitive member which has two photosensitive layers functioning separately as a charge generation layer and a charge transport layer.

Preferably, the charge transport layer in this invention is formed from a solution of the present hydrazone compound and a binder in a suitable solvent by coating and drying. For the binder, a wide variety of resins can be used, for example, polyarylate, polysulfone, polyamide, acrylic resin, polyacrylonitrile resin, polystyrene resin, methacrylic resin, polyvinyl chloride resin, polyvinyl acetate resin, phenolic resin, epoxy resin, polyester resin, alkyd resin, polycarbonate, polyurethane, cellulose ester resin, cellulose ether resin, and copolymers of the monomers constituting said polymers, and of the monomer and butadiene such as styrene-butadiene copolymer, styrene-acrylonitrile copolymer, and styrene-maleic acid copolymer. Besides these insulating polymers, organic photoconductive polymers can also be used, including polyvinylcarbazole, polyvinylanthracene, polyvinylpyrene, etc.

Suitable compounding ratios of the hydrazone compound to the binder are from 10:100 to 500:100 by weight.

The charge transport layer electrically contacts with the charge generation layer, which will be described later in detail, and has the function of receiving the charge carriers injected from the charge generation layer in an electric field and the function of transporting the charge carriers to its surface. The charge transport layer may be laminated on either side of the charge generation layer, i.e., upper or lower surface thereof, but preferably on the upper surface. Since the charge carrier transport distance possible to the charge transport layer is limited, the thickness of this layer cannot be made larger than is necessary. The thickness ranges generally from 5 to 30μ, preferably from 8 to 20μ.

Solvents suitable for use in the formation of the charge transport layer vary depending upon the kind of binders used and are selected from those which do not dissolve the charge generation layer or the undercoating layer mentioned later. Examples of the solvent are alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate and ethyl acetate; halogenated aliphatic hydrocarbons such as chloroform, methylene chloride, dichloroethylene, carbon tetrachloride, and trichloroethylene; and aromatic hydrocarbons or chlorinated derivatives thereof such as benzene, toluene, xylene, ligroin, monochlorobenzene, and dichlorobenzene.

The coating can be carried out by various coating methods such as dip coating, spray coating, spinner coating, bead coating, Meyer bar coating, blade coating, roller coating, curtain coating, etc. Preferably, the coating, after dried to the touch at a room temperature, is dried by heating at a temperature of 30°-200° C. for 5 minutes-2 hours with or without blowing air.

Various additives can be incorporated in the charge transport layer. Such additives include, for example, diphenyl, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiodipropionate, 3,5-dinitrosalycilic acid, and various fluorocarbons.

The charge generation layer in this invention can be made up of a vapor deposition film of a charge-generating material or a coating film of a charge-generating material dispersed in a resin. The charge-generating material can be selected from selenium, selenium-tellurium, pyrylium or co-crystalline complexes thereof, thiapyrylium dyes or co-crystalline complexes thereof, phthalocyanine dyes, anthranthrone pigments, dibenzpyrenequinone pigments, pyranthrone pigments, trisazo pigments, disazo pigments, monoazo pigments, indigo pigments, quinacridone pigments, asymmetric or symmetric quinocyanine pigments, and amorphous silicon, which has been disclosed in Japanese Patent Laid-open No. 143645/1979. Examples of the charge-generating materials inorganic and organic are listed below.

Charge-generating Materials (1) Amorphous silicon
(2) Selenium-tellurium
(3) Selenium-arsenic
(4) Cadmium sulfide (5)

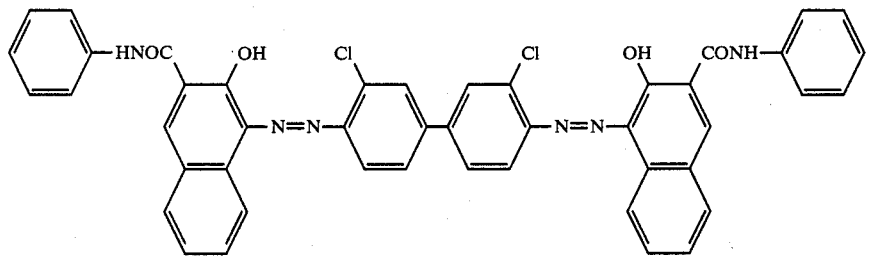

(6)

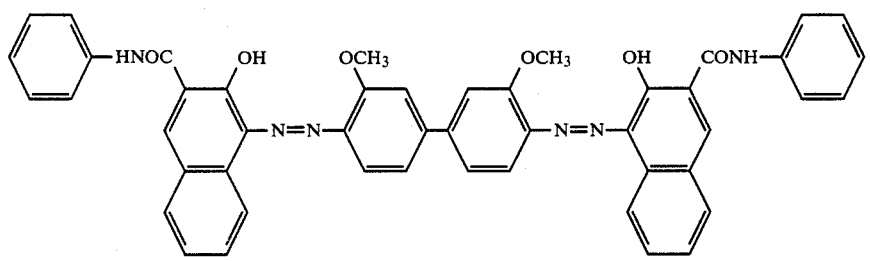

(7)

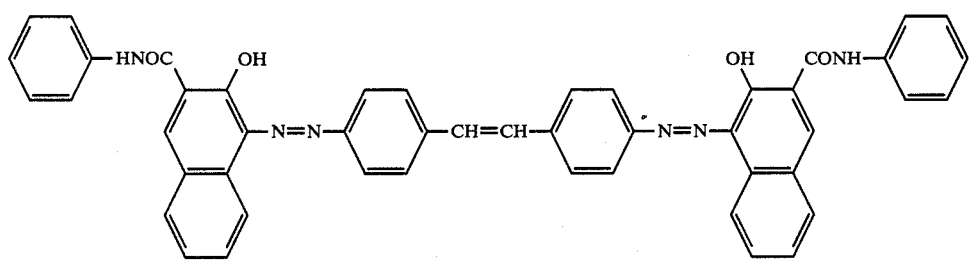

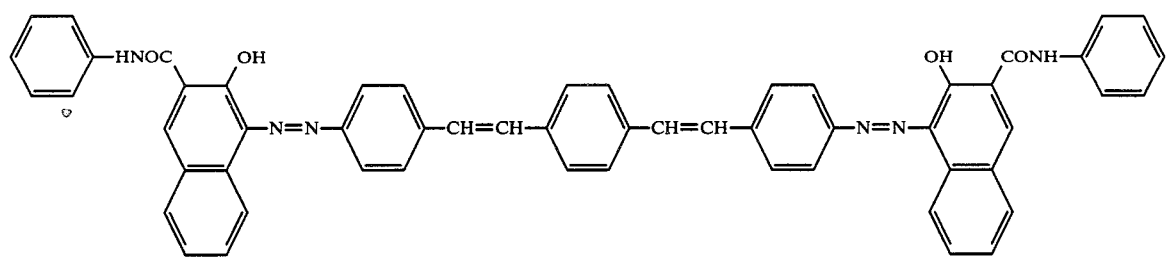 (8)
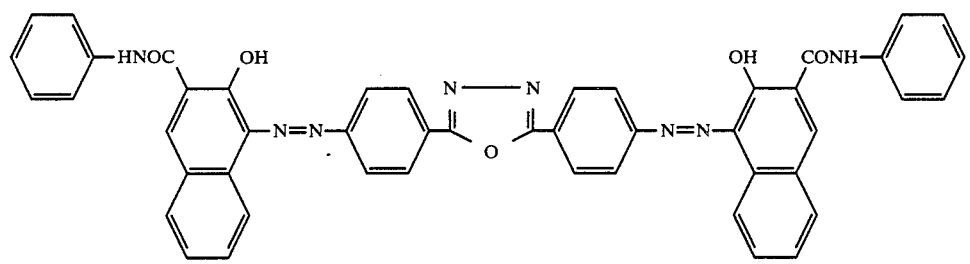 (9)
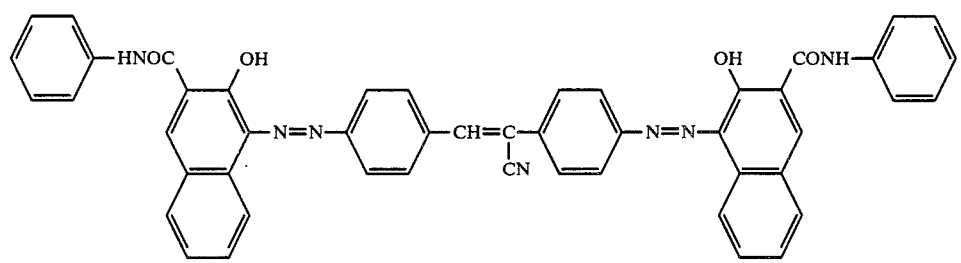 (10)
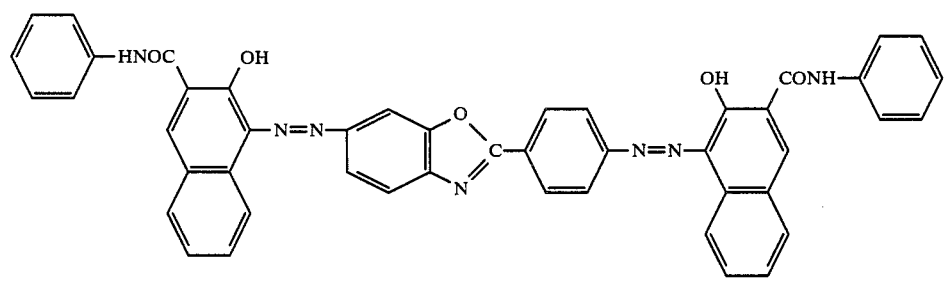 (11)
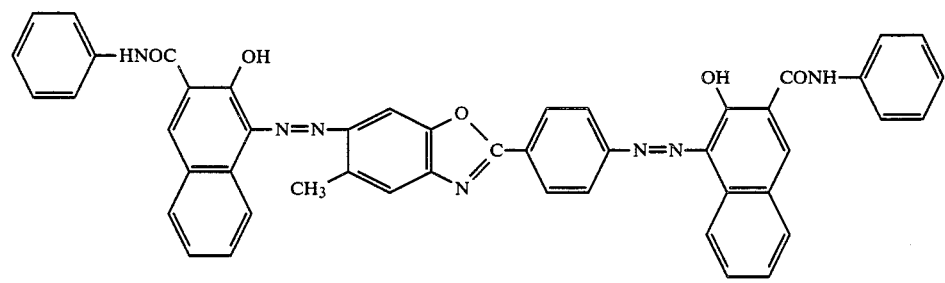 (12)

-continued
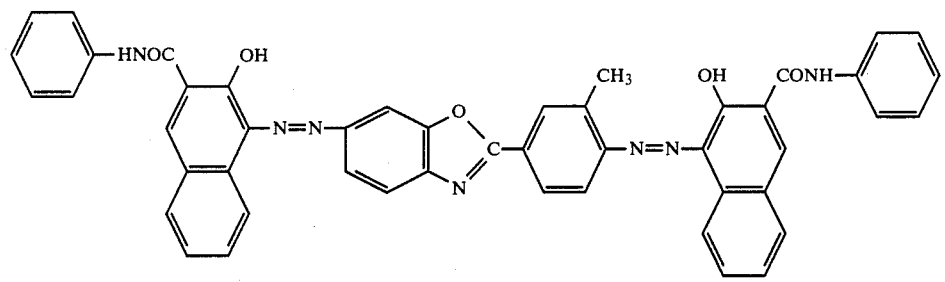
(13)
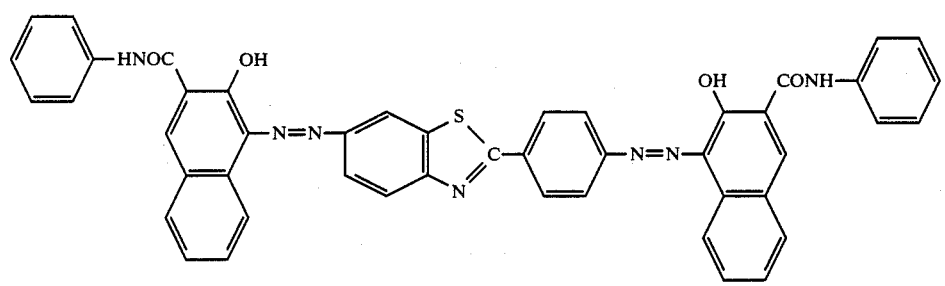
(14)
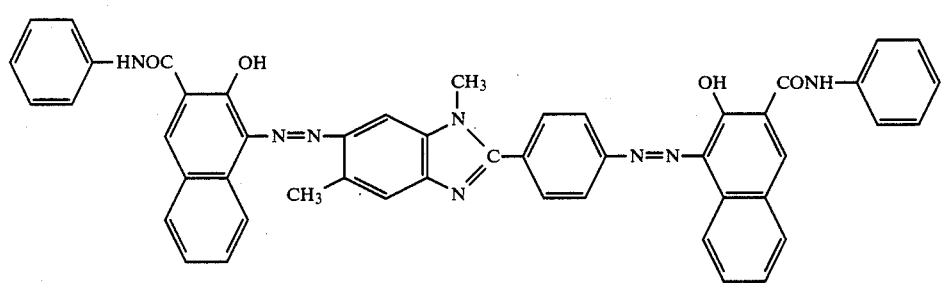
(15)
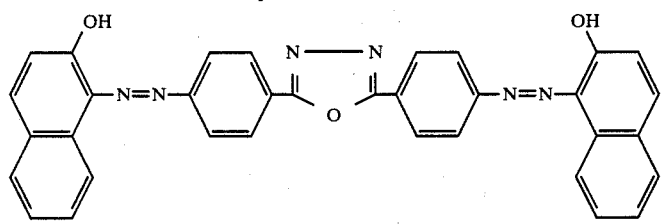
(16)
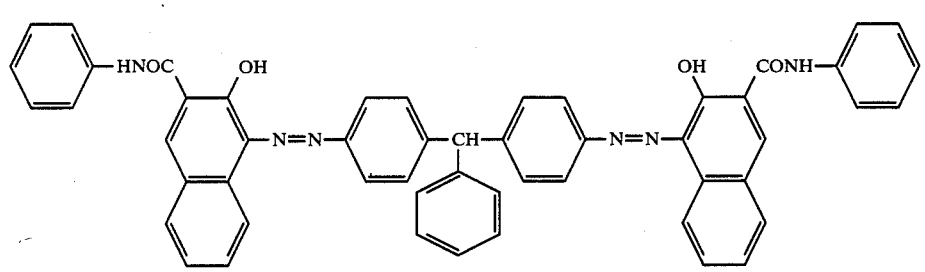
(17)
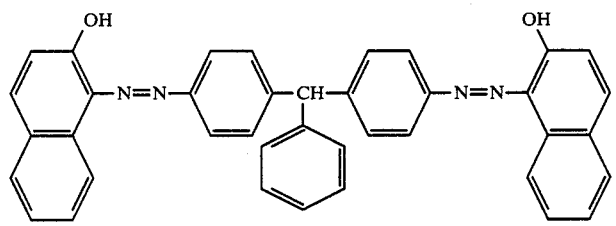
(18)

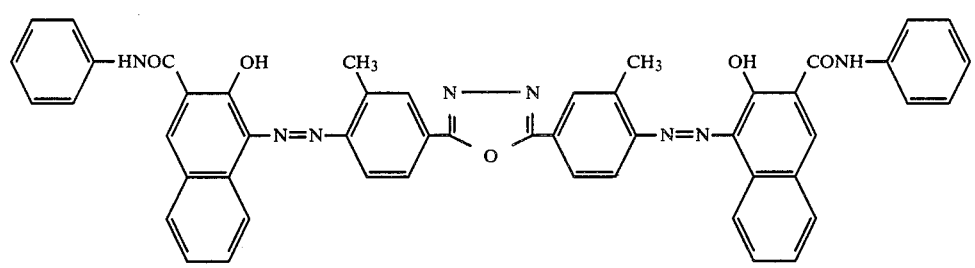
(19)
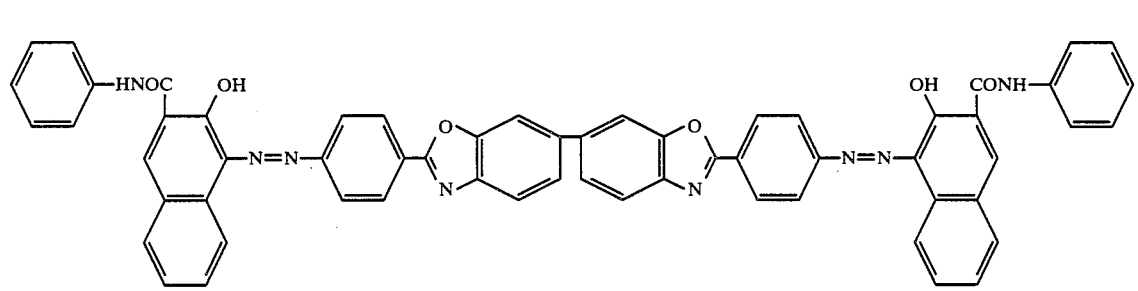
(20)
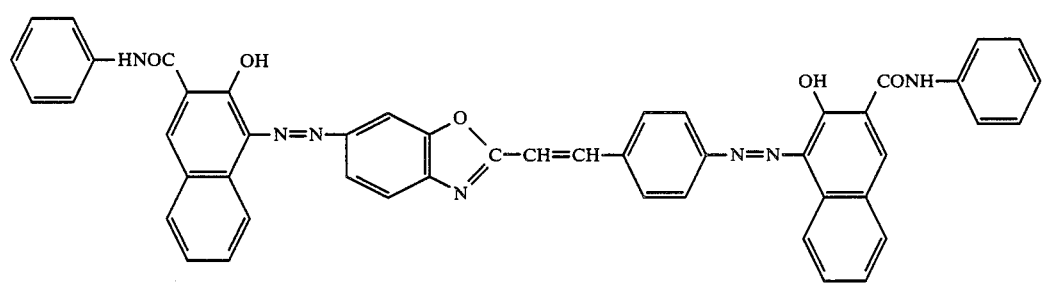
(21)
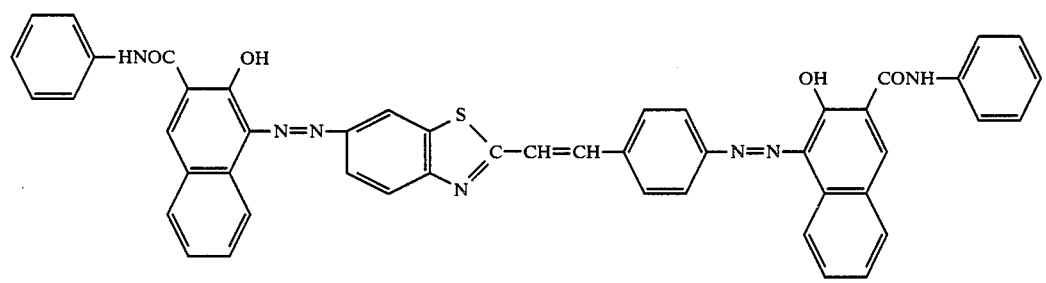
(22)
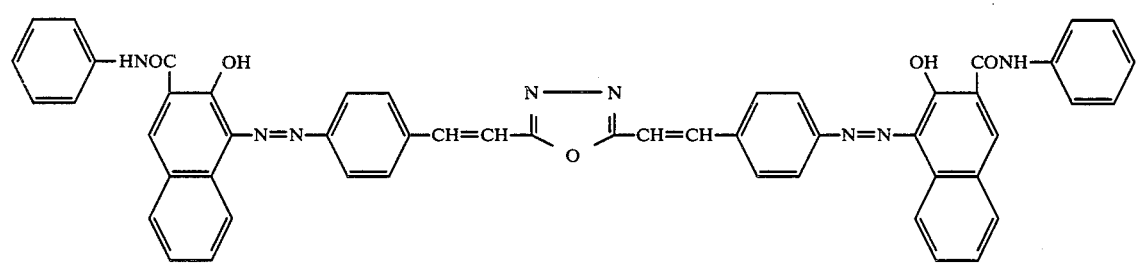
(23)

-continued
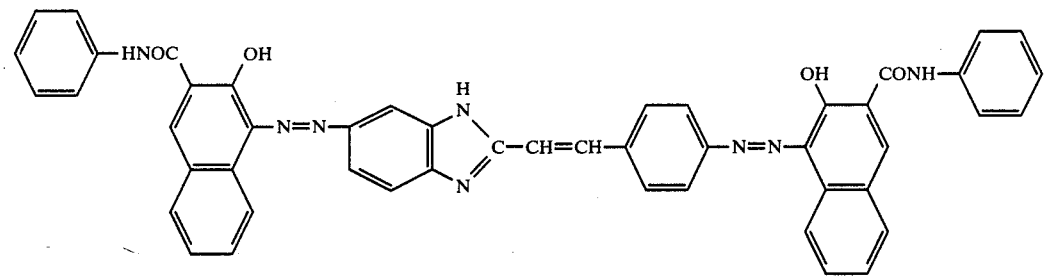
(24)
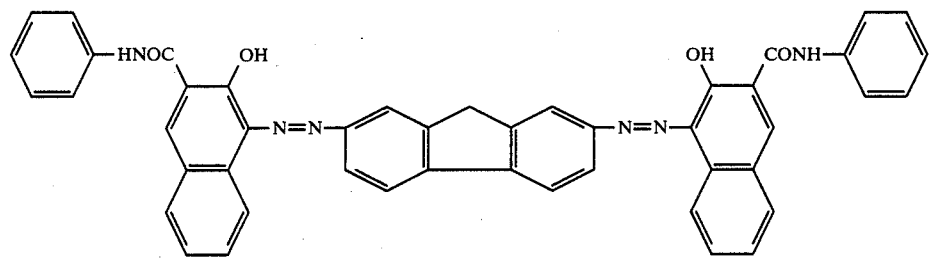
(25)
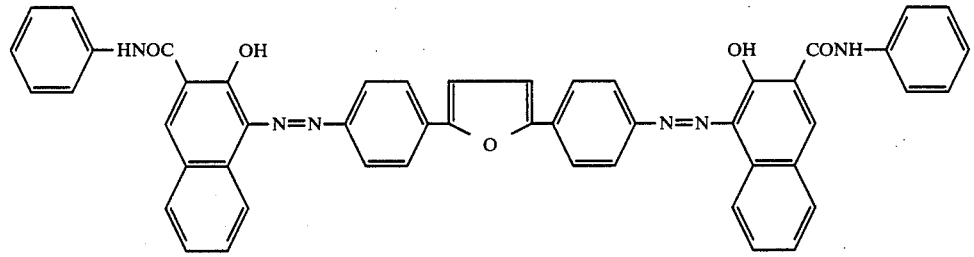
(26)
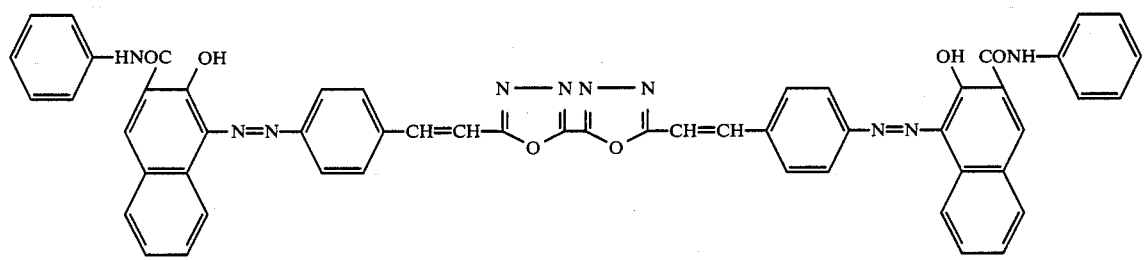
(27)
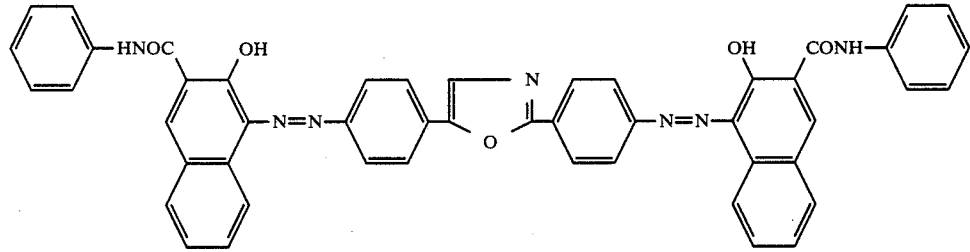
(28)
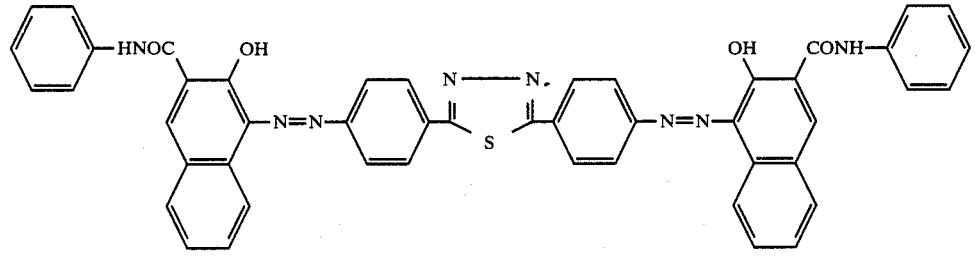
(29)

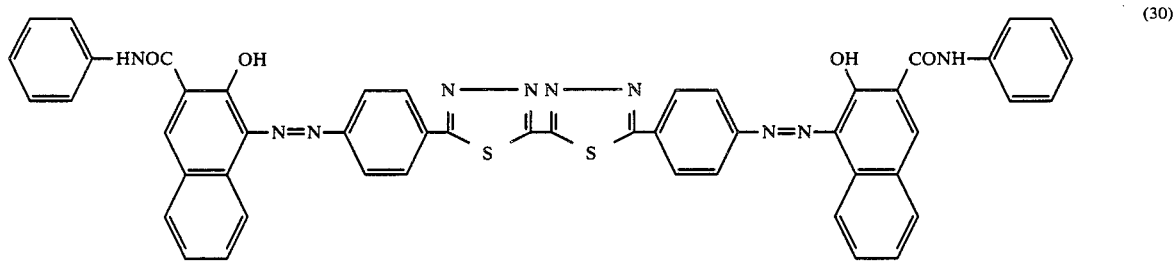
(30)
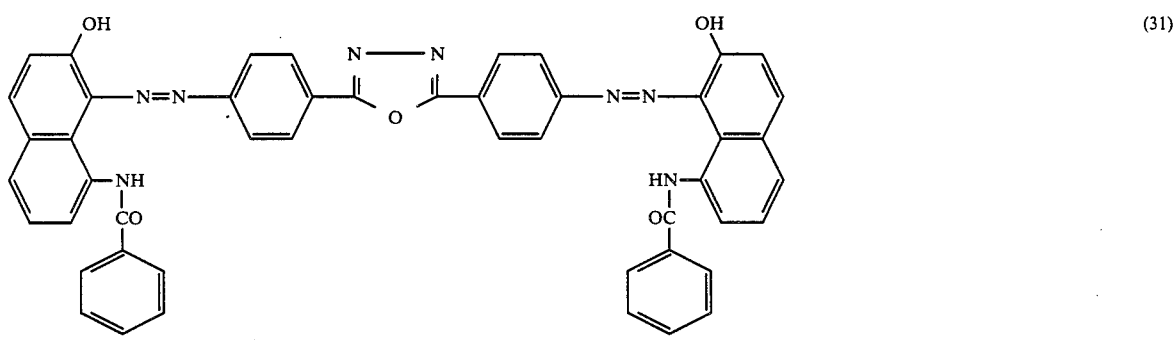
(31)
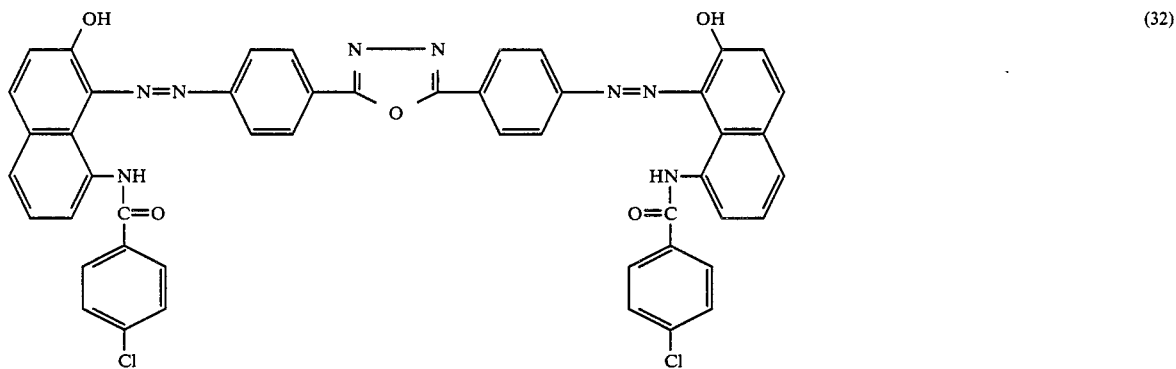
(32)
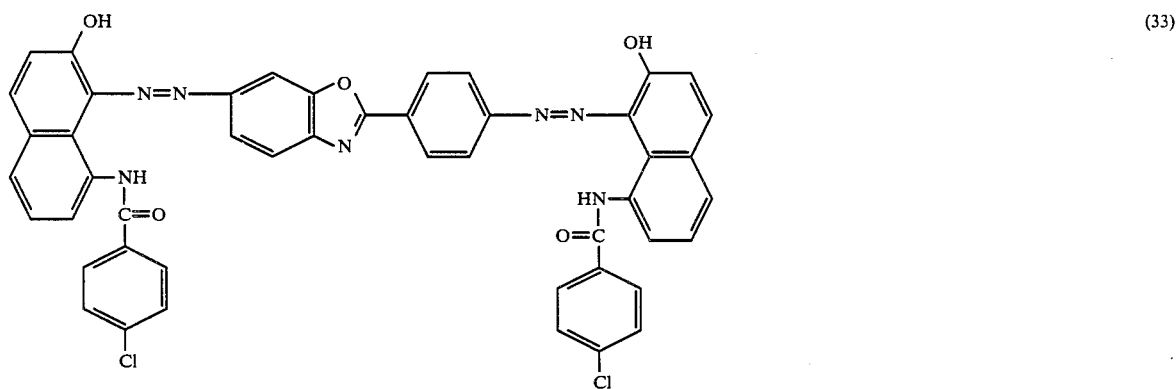
(33)

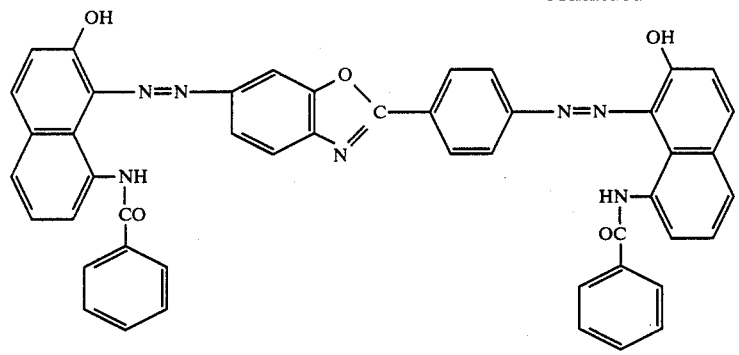
(34)
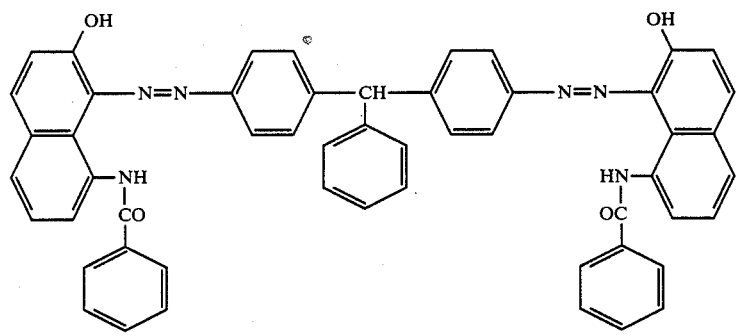
(35)
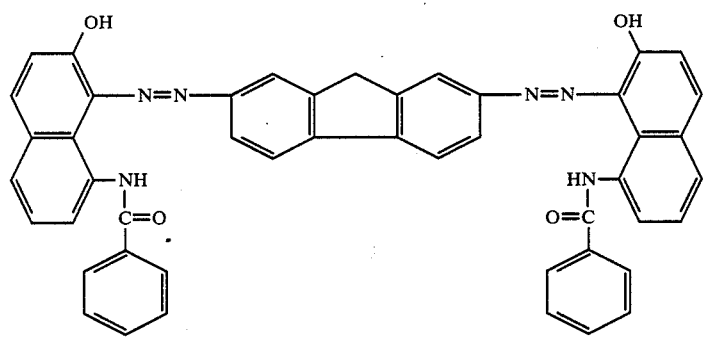
(36)
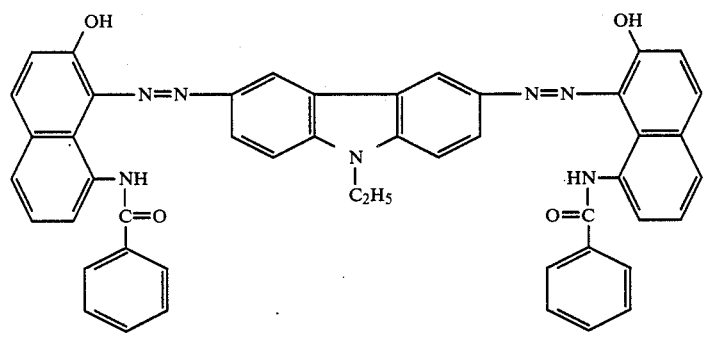
(37)
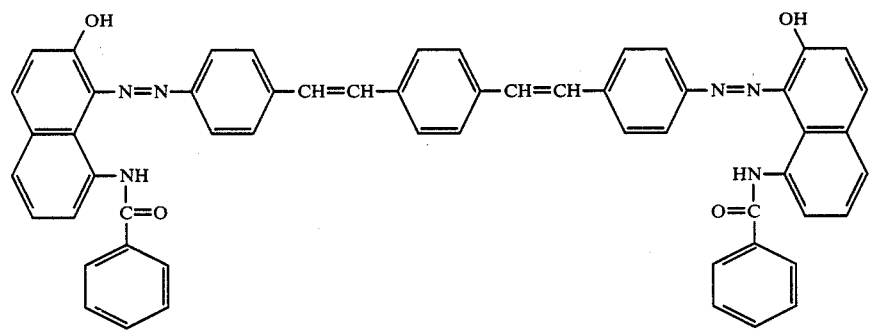
(38)

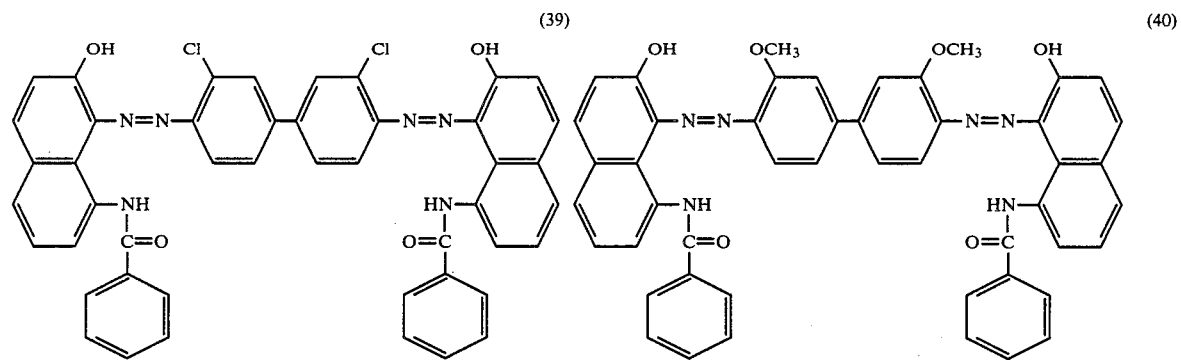
(39) (40)
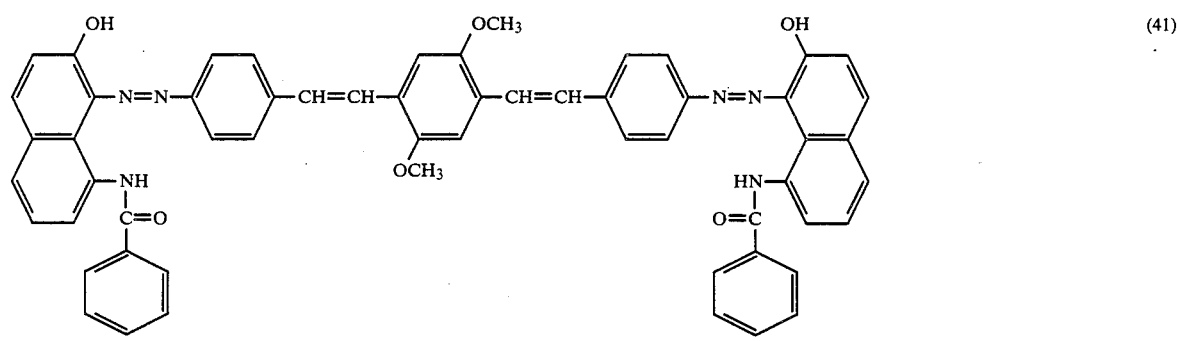
(41)
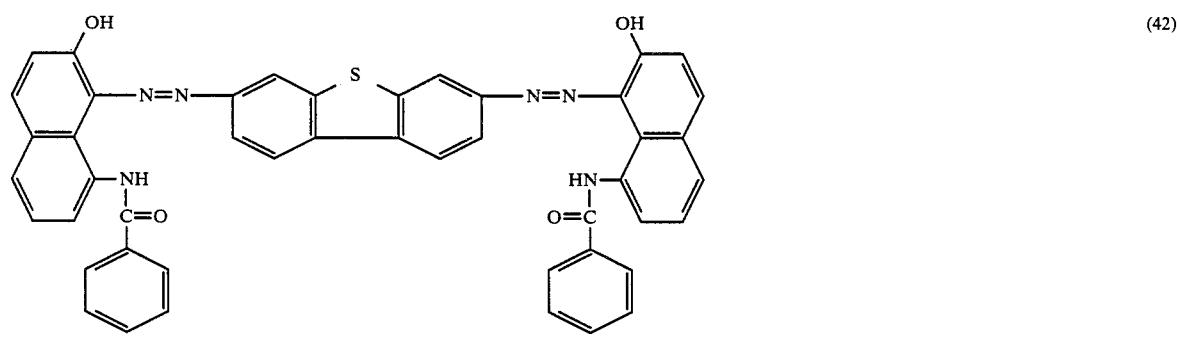
(42)
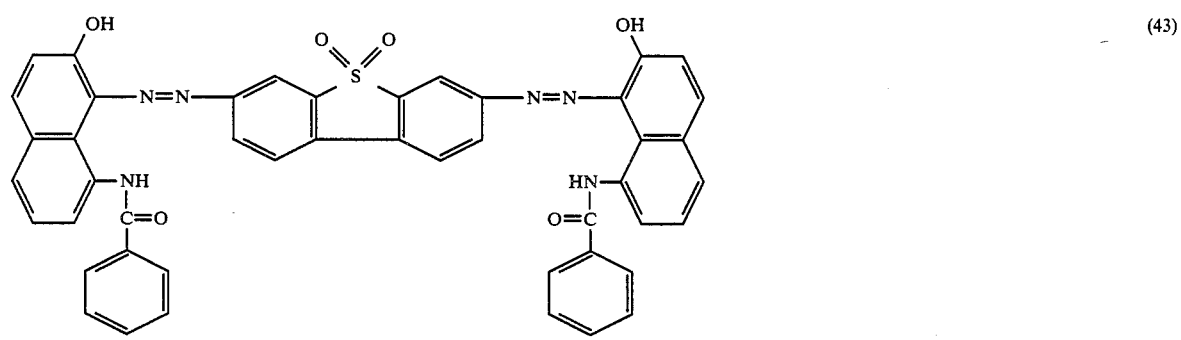
(43)

-continued
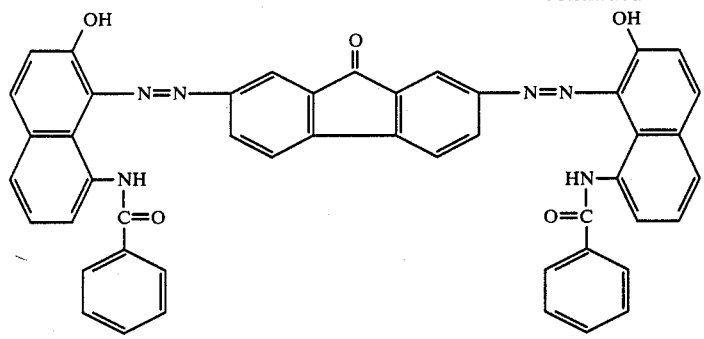
(44)
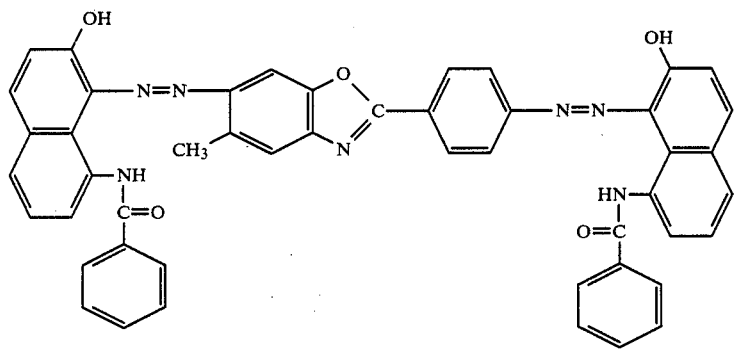
(45)
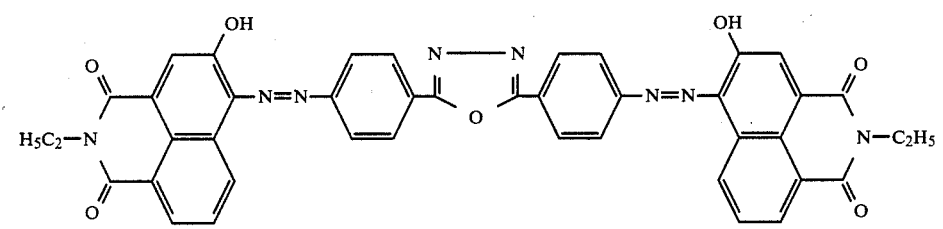
(46)
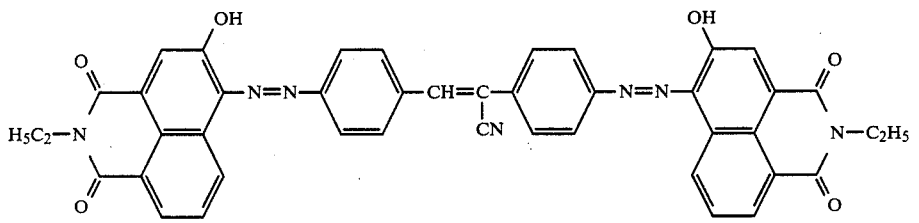
(47)
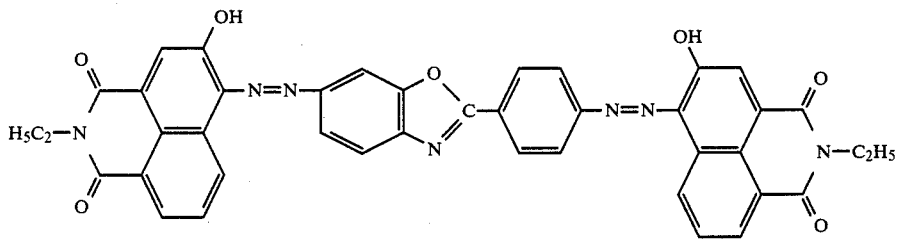
(48)
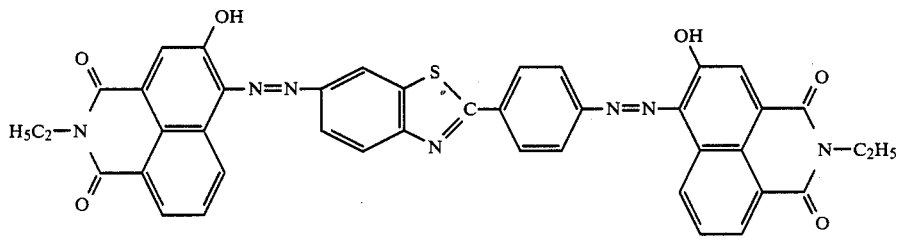
(49)

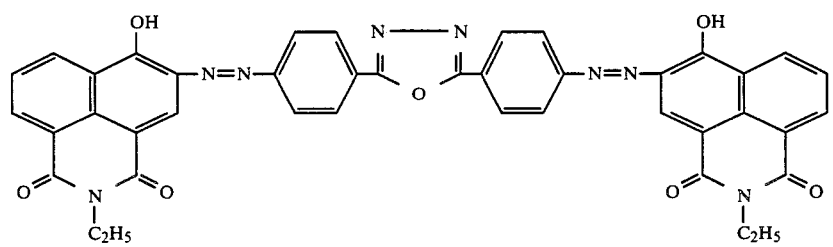 (50)
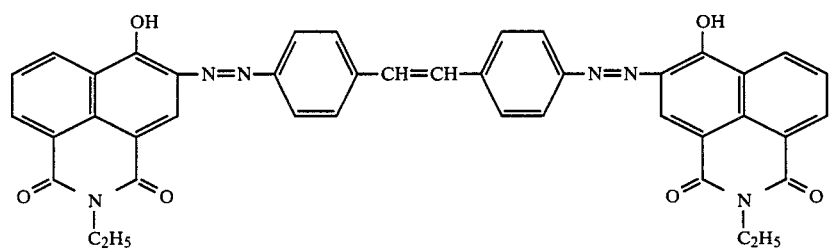 (51)
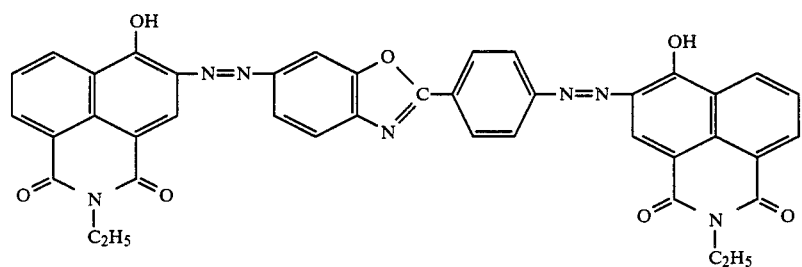 (52)
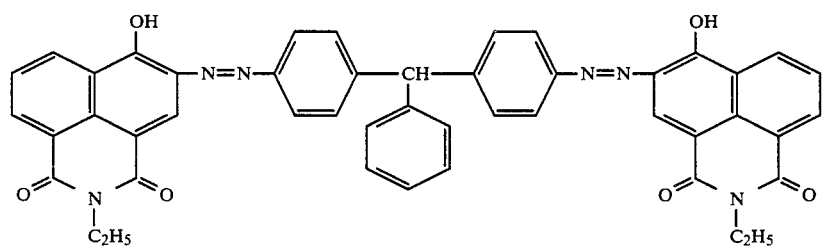 (53)
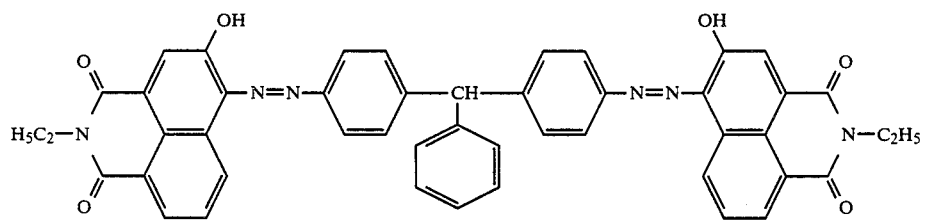 (54)
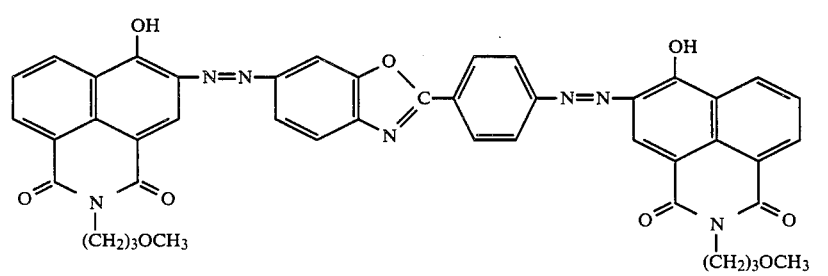 (55)

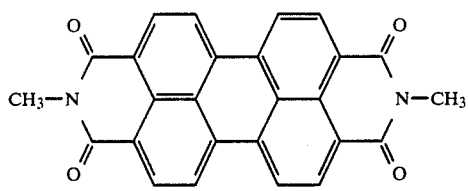
(56)

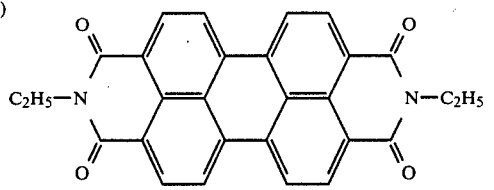
(57)

(58) Methine dye derived from squaric acid
(59) Indigo dye (C.I. No. 78000)
(60) Thioindigo dye (C.I. No. 78800)
(61) β-Type of copper phthalocyanine

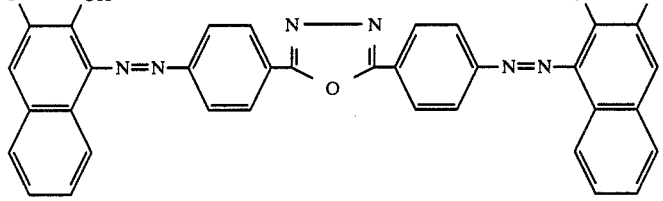
(62)

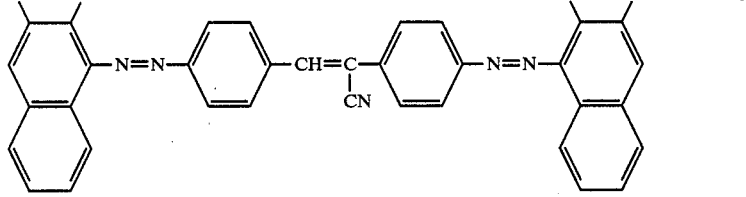
(63)

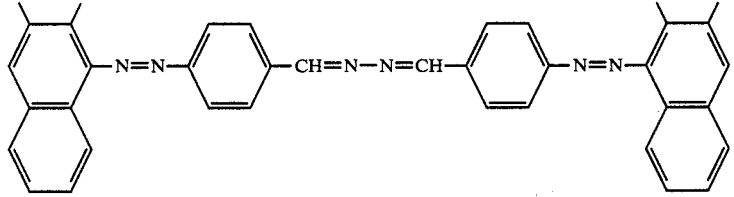
(64)

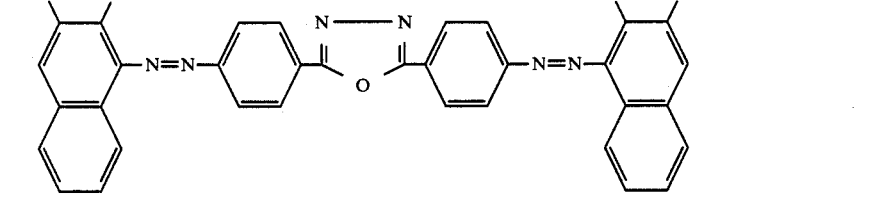
(65)

The charge generation layer can be formed by coating a dispersion of the above charge-generating material in a solution of a suitable binder on a substrate or by vapor deposition of the charge-generating material in a vacuum evaporation apparatus. The binder can be selected from a wide variety of insulating resins and from organic photoconductive polymers such as poly-N-vinylcarbazole, polyvinylanthracene, and polyvinylpyrene. Preferred examples of the binder are insulating resins such as poly(vinyl butyral), polyarylate (e.g. a bisphenol A-phthalic acid polycondensate), polycarbonate, polyester, phenoxy resin, polyvinylacetate, acrylic resin, polyacrylamide polyamide, polyvinylpyridine, cellulosic resin, urethane resin, epoxy resin, casein, polyvinyl alcohol, and polyvinylpyrrolidone. The binder content in the charge generation layer is up to 80%, preferably up to 40%, by weight.

Solvents suitable for use in the coating include, for example, alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethylsulfoxide; ethers such as tetrahydrofuran, dioxane, and ethylene glycol monomethyl ether; esters such as methyl acetate and ethyl acetate; halogenated aliphatic hydrocarbons such as chloroform, methylene chloride, dichloroethane, carbon tetrachloride, and trichloroethylene; and aromatic hydrocarbons or chlorinated derivatives thereof such as benzene, toluene, xylene, ligroin, monochlorobenzene, and dichlorobenzene.

Coating methods applicable in this case are dip coating, spray coating, spinner coating, bead coating, Meyer bar coating, blade coating, roller coating, curtain coating, etc.

The charge generation layer is desired to contain the above-cited charge-generating material as much as possible to absorb a sufficient quantity of light and is also desired to be as thin as up to $5\mu$, preferably $0.01-1.0\mu$, for the purpose of shortening the maximum distance necessary for generated charge carriers to reach the charge transport layer. This is because the charge generation layer needs to absorb most of the incident light and form many charge carriers and further because the formed charge carriers need to be injected into the charge transport layer without deactivation due to the recombination or the trapping.

The photosensitive laminate consisting of the charge generation and charge transport layers is supported by a substrate having a conductive layer. Suitable substrates include sheets or the like of metals, electrically conductive in themselves, for example, aluminum, aluminum alloy, copper, zinc, stainless steel, vanadium, molybdenum, chromium, titanium, nickel, indium, gold, and platinum; those of plastics, for example, polyethylene, polypropylene, polyvinyl chloride, polyethylene terephthalate, acrylic resin, and polyfluoroethylene, which have a conductive coating layer formed by vacuum deposition of aluminum, aluminum alloy, indium oxide, tin oxide, indium oxide-tin oxide alloy, or the like; those of plastics coated with conductive particles, for example, carbon black, silver particles, or the like; those of plastics and paper impregnated with conductive particles; and those of plastics containing a conductive polymer.

An undercoating layer can be laid between the conductive layer and the laminated photosensitive layer. This undercoating layer can be made of, for example, casein, polyvinyl alcohol, nitrocellulose, ethylene-acrylic acid copolymer, polyamides (nylon 6, nylon 66, nylon 610, copolymerized nylon, alkoxymethylated nylon, etc.), polyurethane, gelatin, or aluminum oxide.

Suitable thickness of the undercoating layer ranges from 0.1 to $5\mu$, preferably from 0.5 to $3\mu$.

When the photosensitive member comprising a conductive layer, charge generation layer, and charge transport layer laminated in that order is operated, the surface of the charge transport layer needs to be negatively charged since the hydrazone compound used in a hole-transporting material. On image exposure of the photosensitive member after charging, holes produced in the charge generation layer, in the exposed region, are injected into the charge transport layer, then arrive at the surface, and neutralize the negative charge to decay the surface potential, thus forming an electrostatic contrast to the unexposed region. For developing this, a positive-working toner needs to be used in this case contrary to the case where the charge transporting material employed is electron-transporting.

In another embodiment of this invention, a photoconductive pigment or dye can be used as a sensitizer or charge-generating material in the photoconductive layer containing the present hydrazone compound. Examples of this pigment or dye are the above-cited diasazo pigments and pyrylium group dyes, as disclosed in U.S. Pat. Nos. 3,554,745, 3,567,438, and 3,586,500 and other literature, such as pyrylium, thiapyrylium, selenapyrylium, benzopyrylium, benzothiapyrylium, naphthopyrylium, and naphthothiapyrylium dyes.

In a further embodiment of this invention, a co-crystalline complex of a pyrylium dye with an insulating polymer containing alkylidenediarylene groups, as disclosed in U.S. Pat. No. 3,684,502, can be used as a sensitizer or charge-generating material in the photoconductive layer. This co-crystalline complex can be obtained in gracular form by dissolving, for example, 4-[4-bis(2-chloroethyl)aminophenyl]-2,6-diphenylthiapyrylium perchlorate and poly(4,4'-isopropylidenediphenylene carbonate) in a halogenated hydrocarbon solvent (e.g. dichloromethane, chloroform, carbon tetrachloride, 1,1-dichloroethane, 1,2-dichloroethane, 1,1,2-trichloroethane, chlorobenzene, bromobenzene, or 1,2-dichlorobenzene) and adding a nonpolar solvent (e.g. hexane, octane, decane, 1,2,4-trimethylbenzene, or ligroin) to the solution. In the photoconductive layer of this type of photosensitive member, a binder can be incorporated such as styrene-butadiene copolymer, silicone resins, vinyl resins, vinylidene chloride-acrylonitrile copolymer, styrene-acrylonitrile copolymer, vinyl acetate-vinyl chloride copolymer, polyvinylbutyral, polymethyl methacrylate, poly-n-butyl methacrylate, polyester, cellulose ester, or the like.

The electrophotographic photosensitive member of this invention can be used not only in electrophotographic copying machines but also over a wide field of electrophotographic applications such as those to laser printers, CRT printers, and electrophotographic printing plate making systems.

According to this invention, it is possible to provide a high sensitivity electrophotographic photosensitive member which shows limited variations in the light area and dark area potentials when the charging and exposing are repeated many times and which is improved in the photomemory property.

This invention will be illustrated in more detail referring to the following Examples:

EXAMPLE 1

A $\beta$-type of copper phthalocyanine (tradename: Lionol Blue NCB Toner, mfd. by Toyo Ink Mfg. Co., Ltd.) was purified by heating successively in water, ethanol, and benzene under reflux, followed by filtration. A coating dispersion was prepared by grinding 7 g of the purified pigment in a mixture of 14 g of Polyester Adhesive 49,000 (a polyester solution, 20% solid, mfg. by Du Pont de Nemours & Co.), 35 g of toluene, and 35 g of dioxane with a ball mill for 6 hours. The dispersion was applied on an aluminum sheet by use of a Meyer bar and dried to form a charge generation layer $0.5\mu$ thick.

A solution prepared by dissolving 7 g of the above-cited hydrazone compound H-(1) and 7 g of a polycarbonate resin (Panlite K-1300, mfd. by Teijin Kasei Co., Ltd.) in a mixture of 35 g of tetrahydrofuran and 35 g of monochlorobenzene was applied on the charge generation layer by means of a Meyer bar and dried to form a charge transport layer $11\mu$ thick.

The electrophotographic photosensitive member of two laminar structure thus prepared was corona-charged at $-5$ KV in the static fashion by using an electrostatic copying paper testing machine (Model SP-428, mfd. by Kawaguchi Denki Co., Ltd.), then was retained for 10 seconds in the dark, and exposed to light at an intensity of 5 lux, to examine charge bearing characteristics of the photosensitive member.

The charge bearing characteristics examined were the initial surface potential ($V_0$) at the corona charging, the surface potential ($V_1$) after 10-second dark decay, and the exposure quantity ($E_{1/2}$) for halving the initial surface potential.

For further measurement of variations in the light area and dark area potentials during repeated operations, the photosensitive member was attached around the cylinder of an electrophotographic copying machine which was provided with a −5.6 KV corona charger, optical system for 10-lux.sec.light exposure, developing device, charger for transfer copying, optical system for light exposure to eliminate the residual charge, and cleaner. Thus, this copying machine forms an image on a sheet of transfer paper for each revolution of the cylinder. Using this copying machine, the light area potential ($V_L$) and dark area potential ($V_D$) were determined at the initial charging and at the 5000th charging in continuous repeated operations. These results were as follows:

| | | |
|---|---|---|
| $V_0$: | −570 V | |
| $V_1$: | −555 V | |
| $E_{\frac{1}{2}}$: | 5.2 lux.sec | |
| | Initial charging | 5000th charging |
| $V_L$: | −70 V | −70 V |
| $V_D$: | −645 V | −635 V |

EXAMPLES 2-30

Electrophotographic photosensitive members were prepared in the same manner as in Example 1 except using different hydrazone compounds as charge-transporting materials. Results of the same tests on these photosensitive members as in Example 1 are shown in Tables 1 and 2.

TABLE 1

| Example No. | Hydrazone compound | $E_{\frac{1}{2}}$ (lux.sec) | $V_0$ (−volt) | $V_1$ (−volt) |
|---|---|---|---|---|
| 2 | H-(2) | 5.8 | 550 | 540 |
| 3 | H-(3) | 5.4 | 565 | 560 |
| 4 | H-(4) | 7.3 | 580 | 570 |
| 5 | H-(5) | 7.1 | 565 | 565 |
| 6 | H-(6) | 4.8 | 555 | 550 |
| 7 | H-(7) | 5.5 | 565 | 555 |
| 8 | H-(8) | 6.6 | 575 | 555 |
| 9 | H-(9) | 4.0 | 560 | 545 |
| 10 | H-(10) | 5.4 | 570 | 565 |
| 11 | H-(11) | 4.9 | 550 | 535 |
| 12 | H-(12) | 4.7 | 570 | 555 |
| 13 | H-(13) | 3.3 | 545 | 525 |
| 14 | H-(14) | 3.9 | 550 | 525 |
| 15 | H-(16) | 3.6 | 580 | 560 |
| 16 | H-(17) | 3.3 | 590 | 585 |
| 17 | H-(18) | 3.2 | 560 | 555 |
| 18 | H-(19) | 4.4 | 565 | 566 |
| 19 | H-(20) | 4.8 | 585 | 580 |
| 20 | H-(22) | 3.9 | 590 | 580 |
| 21 | H-(23) | 5.2 | 575 | 565 |
| 22 | H-(24) | 5.3 | 595 | 590 |
| 23 | H-(25) | 3.7 | 590 | 575 |
| 24 | H-(26) | 3.5 | 600 | 595 |
| 25 | H-(28) | 3.7 | 565 | 560 |
| 26 | H-(30) | 4.2 | 570 | 560 |
| 27 | H-(31) | 2.9 | 565 | 555 |
| 28 | H-(32) | 3.4 | 575 | 570 |
| 29 | H-(34) | 3.0 | 555 | 545 |
| 30 | H-(36) | 2.7 | 560 | 545 |

TABLE 2

| Example No. | Hydrazone compound | Initial charging | | 5000th charging | |
|---|---|---|---|---|---|
| | | $V_L$ (−volt) | $V_D$ (−volt) | $V_L$ (−volt) | $V_D$ (−volt) |
| 2 | H-(2) | 75 | 635 | 75 | 630 |
| 3 | H-(3) | 65 | 625 | 75 | 625 |
| 4 | H-(4) | 95 | 650 | 105 | 640 |
| 5 | H-(5) | 90 | 645 | 100 | 635 |
| 6 | H-(6) | 60 | 635 | 75 | 630 |
| 7 | H-(7) | 75 | 645 | 80 | 630 |
| 8 | H-(8) | 90 | 655 | 95 | 650 |
| 9 | H-(9) | 45 | 635 | 60 | 630 |
| 10 | H-(10) | 85 | 660 | 90 | 645 |
| 11 | H-(11) | 50 | 625 | 60 | 615 |
| 12 | H-(12) | 70 | 645 | 75 | 635 |
| 13 | H-(13) | 25 | 615 | 40 | 600 |
| 14 | H-(14) | 40 | 630 | 60 | 615 |
| 15 | H-(16) | 35 | 660 | 40 | 640 |
| 16 | H-(17) | 20 | 640 | 30 | 630 |
| 17 | H-(18) | 30 | 655 | 40 | 645 |
| 18 | H-(19) | 35 | 625 | 50 | 620 |
| 19 | H-(20) | 60 | 665 | 70 | 660 |
| 20 | H-(22) | 25 | 645 | 40 | 625 |
| 21 | H-(23) | 80 | 670 | 90 | 670 |
| 22 | H-(24) | 55 | 645 | 65 | 635 |
| 23 | H-(25) | 35 | 660 | 45 | 650 |
| 24 | H-(26) | 35 | 660 | 50 | 645 |
| 25 | H-(28) | 50 | 675 | 65 | 670 |
| 26 | H-(30) | 45 | 620 | 60 | 610 |
| 27 | H-(31) | 15 | 645 | 30 | 630 |
| 28 | H-(32) | 40 | 665 | 45 | 650 |
| 29 | H-(34) | 25 | 670 | 45 | 660 |
| 30 | H-(36) | 15 | 650 | 25 | 640 |

EXAMPLE 31

A coating dispersion was prepared by grinding 5 g of the above-cited hydrazone compound H-(15) and 3 g of 4-(4-dimethylaminophenyl)-2,6-diphenylthiapyrylium perchlorate in a mixture of 5 g of Polyester Adhesive 49000 (the same as used in Example 1), 50 ml of toluene, and 50 ml of dioxane with a ball mill for 6 hours. This dispersion was applied on an aluminum sheet by means of a Meyer bar and dried to form a photoconductive layer 15μ thick.

Results of the same tests on the thus prepared photosensitive member as in Example 1 were as follows:

| | | |
|---|---|---|
| $V_0$: | −560 V | |
| $V_1$: | −555 V | |
| $E_{\frac{1}{2}}$: | 5.0 lux.sec | |
| | Initial charging | 5000th charging |
| $V_L$ | −75 V | −75 V |
| $V_D$ | −670 V | −660 V |

EXAMPLE 32

The same type of photosensitive member was prepared in the same manner as in Example 31 but using the above-cited hydrazone compound H-(21) in place of H-(15). Results of the same tests on this photosensitive member as conducted in Example 1 were as follows:

| | | |
|---|---|---|
| $V_0$: | −560 V | |
| $V_1$: | −550 V | |
| $E_{\frac{1}{2}}$: | 4.3 lux.sec | |
| | Initial charging | 5000th charging |
| $V_L$: | −50 V | −50 V |
| $V_D$: | −610 V | −600 V |

EXAMPLE 33

A solution of casein in aqueous ammonia (casein 11.2 g, 28% aqueous ammonia 1 g, water 222 ml) was applied on an aluminum sheet by use of a Meyer bar and dried to form an undercoating layer 1.0μ thick.

A dispersion of 5 g of a disazo pigment represented by the formula

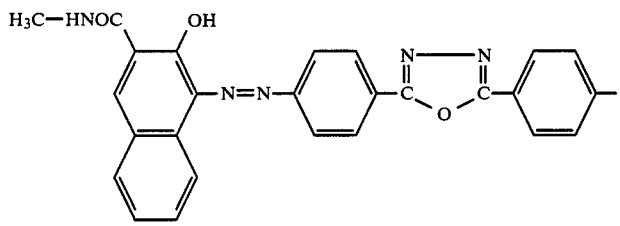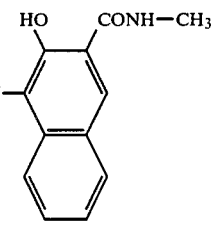

in a solution of 2 g of a vinyl butyral resin (degree of butyral conversion 63 mole%) in 95 ml of ethanol was applied on the undercoating layer and dried to form a charge generation layer 0.4μ thick.

A solution prepared by dissolving 5 g of the above-cited hydrazone compound H-(4) and 5 g of poly-4,4'-dihydroxydiphenyl-2,2-propanecarbonate (viscosity average mol. wt. 30,000) in 150 ml of dichloromethane was applied on the charge generation layer and dried to form a charge transport layer 11μ thick.

Results of the same tests on the thus prepared photosensitive member as in Example 1 were as follows:

| | | |
|---|---|---|
| $V_0$: | −580 V | |
| $V_1$: | −570 V | |
| $E_{\frac{1}{2}}$: | 5.5 lux.sec | |
| | Initial charging | 5000th charging |
| $V_L$: | −65 V | −75 V |
| $V_D$: | −670 V | −660 V |

EXAMPLE 34

The same type of photosensitive member was prepared in the same manner as in Example 33 but using the above-cited hydrazone compound H-(27) in place of H-(4). Results of the same tests on this photosensitive member as conducted in Example 1 were as follows:

| | | |
|---|---|---|
| $V_0$: | −615 V | |
| $V_1$: | −610 V | |
| $E_{\frac{1}{2}}$: | 5.2 lux.sec | |
| | Initial charging | 5000th charging |
| $V_L$: | −75 V | −80 V |
| $V_D$: | −635 V | −625 V |

EXAMPLE 35

A surface-cleaned molybdenum sheet (substrate) 0.2 mm thick was fixed on a prescribed position in a glow discharge chamber for vapor deposition. The chamber was evacuated to a vacuum of about $5 \times 10^{-6}$ torr. Then, the substrate temperature was raised with a electric heater and settled to 150° C. Hydrogen gas and silane gas (15% by volume based on hydrogen) was introduced into the chamber, the pressure of which was kept at 0.5 torr by regulating the gas flow rates and the main valve of the chamber. A 5-MHz high-frequency power was applied to an induction coil to generate a glow discharge in a space, surrounded by the coil, in the chamber, where the input power was adjusted to 30 W. Under these conditions, amorphous silicon was deposited on the substrate to a thickness of 2μ. Then, the high-frequency power source and the heater were switched off to stop the glow discharge. After the substrate had cooled down to 100° C., the hydrogen gas and silane gas valves were shut off, the chamber was once evacuated to $10^{-5}$ torr or less and then returned to the atmospheric pressure state, and the substrate was taken out. Subsequently, the same charge transport layer as of Example 1 was formed on the amorphous silicon layer in the same manner.

The photosensitive member thus obtained was set in a charging-exposing test machine and corona-charged at −6 KV. Immediately thereafter, the photosensitive member was irradiated with a pattern of light from a tungsten lamp through a transmission type of test chart. Then, the surface of the photosensitive member was immediately exposed to a cascade of positive-working toner. Thus, a good toner image was obtained on the surface of the photosensitive member.

EXAMPLE 36

The same charge transport layer consisting of amorphous silicon was formed on a surface-cleaned molybdenum sheet 0.2 mm thick in the same manner as in Example 35.

A charge transport layer was formed on the charge generation in the same manner as in Example 1 but using the above-cited hydrazone compound H-(19) in place of H-(1).

The photosensitive member thus prepared gave a good toner image as a result of the same image forming test as conducted in Example 35.

EXAMPLE 37

After 3 g of 4-(4-dimethylaminophenyl)-2,6-diphenyl-thiapyrylium perchlorate and 3 g of a polycarbonate resin had been completely dissolved in 200 ml of dichloromethane, 100 ml of toluene was added to the solution to precipitate their co-crystalline complex. The precipitate was separated by filtration, dissolved in dichloromethane, and precipitated again by adding 100 ml of n-hexane.

A dispersion was prepared by grinding 5 g of the thus obtained co-crystalline complex with a solution of 2 g of polyvinyl butyral in 95 ml of methanol by means of a ball mill for 6 hours. The dispersion was applied to a casein-coated aluminum sheet by use of a Meyer bar and dried to form a charge generation layer 0.4μ thick.

The same charge transport layer as of Example 1 was formed on the charge generation layer.

Results of the same tests on the thus prepared photosensitive member as conducted in Example 1 were as follows:

| $V_0$: | | −565 V |
|---|---|---|
| $V_1$: | | −545 V |
| $E_{\frac{1}{2}}$: | | 3.3 lux.sec |
| | Initial charging | 5000th charging |
| $V_L$: | −40 V | −55 V |
| $V_D$: | −615 V | −605 V |

EXAMPLE 38

The same type of photosensitive member was prepared in the same manner as in Example 37 but using the above-cited hydrazone compound H-(23) in place of H-(1).

Results of the same tests on this photosensitive member as conducted in Example 1 were as follows:

| $V_0$: | | −550 V |
|---|---|---|
| $V_1$: | | −540 V |
| $E_{\frac{1}{2}}$: | | 2.3 lux.sec |
| | Initial charging | 5000th charging |
| $V_L$: | −15 V | −30 V |
| $V_D$: | −610 V | −605 V |

EXAMPLE 39

The same co-crystalline complex (5 g) as prepared in Example 36, the above-cited hydrazone compound H-(4) (5 g), and a solution of Polyester Adhesive 49,000 (the same as used in Example 1) in 150 ml of tetrahydrofuran were thoroughly mixed. The mixture was applied to an aluminum sheet by use of a Meyer bar and dried to form a photoconductive layer 15μ thick.

Results of the same tests on the thus prepared photosensitive member as conducted in Example 1 were as follows:

| $V_0$: | | −550 V |
|---|---|---|
| $V_1$: | | −535 V |
| $E_{\frac{1}{2}}$: | | 3.7 lux.sec |
| | Initial charging | 5000th charging |
| $V_L$: | −40 V | −55 V |
| $V_D$: | −630 V | −615 V |

EXAMPLE 40

The same type of photosensitive member as of Example 39 was prepared in the same manner but using the above-cited hydrazone compound H-(35) in place of H-(4). Results of the same tests on this photosensitive member as conducted in Example 1 were as follows:

| $V_0$: | | −570 V |
|---|---|---|
| $V_1$: | | −565 V |
| $E_{\frac{1}{2}}$: | | 2.6 lux.sec |
| | Initial charging | 5000th charging |
| $V_L$: | −25 V | −35 V |
| $V_D$: | −630 V | −620 V |

What is claimed is:

1. An electrophotographic photosensitive member having a conductive substrate, a charge generation layer, and a charge transport layer, characterized in that the charge transport layer comprises a binder and at least one hydrazone compound represented by the following general formula (1) or (2):

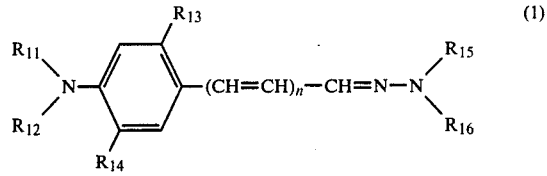

(1)

wherein $R_{11}$ and $R_{12}$ independently of each other represent alkyl, aralkyl, phenyl, alkyl substituted by alkoxy, halogen or dialkylamino, aralkyl substituted by alkyl, alkoxy, halogen or dialkylamino, phenyl substituted by alkyl, alkoxy, halogen or dialkylamino, or $R_{11}$ and $R_{12}$ form a 5- or 6-membered ring residue conjointly with the nitrogen atom to which they are bonded; $R_{13}$ and $R_{14}$ independently of each other represent alkyl or alkoxy; $R_{15}$ and $R_{16}$ independently of each other represent alkyl, aralkyl, aryl, aralkyl substituted by alkyl, alkoxy, halogen or dialkylamino, or aryl substituted by alkyl, alkoxy, halogen or dialkylamino; and n represents an integer of 0 or 1, and

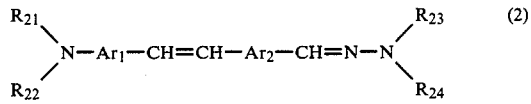

(2)

wherein $R_{21}$ and $R_{22}$ independently of each other represent alkyl, aralkyl, phenyl, alkyl substituted by alkoxy, halogen or dialkylamino, aralkyl substituted by alkyl, alkoxy, halogen or dialkylamino, phenyl substituted by alkyl, alkoxy, halogen or dialkylamino, or $R_{21}$ and $R_{22}$ form a 5- or 6-member ring residue conjointly with the nitrogen atom to which they are bonded; $R_{23}$ and $R_{24}$ independently of each other represent alkyl, aralkyl, aryl, alkyl substituted by alkoxy, halogen or dialkylamino, aralkyl substituted by alkyl, alkoxy, halogen or dialkylamino; and $Ar_1$ and $Ar_2$ independently of each other represent arylene or arylene substituted by alkyl, alkoxy or halogen.

2. The electrophotographic photosensitive member according to claim 1, wherein the charge transport layer is laid on the upper side of the charge generation layer.

3. The electrophotographic photosensitive member according to claim 1, wherein the binder in the charge transport layer is at least one resin selected from the group consisting of polyarylate, polysulfone, polyamide, polystyrene, acrylic resin, methacrylic resin, polyacrylonitrile resin, polyvinyl chloride resin, polyvinyl acetate resin, phenolic resin, epoxy resin, polyester resin, alkyd resin, polycarbonate, polyurethane, a copolymer of monomers constituting said resins, a copolymer of butadiene and a monomer constituting said resins, cellulose ester resin, and cellulose ether resin.

4. The electrophotographic photosensitive member according to claim 1, wherein the charge transport layer contains a photoconductive polymer.

5. The electrophotographic photosensitive member according to claim 1, wherein the charge transport layer contains 10–500 parts by weight of said hydrazone compound for each 100 parts by weight of the binder.

6. The electrophotographic photosensitive member according to claim 1, wherein the charge transport layer has a thickness of 5–30μ.

7. The electrophotographic photosensitive member according to claim 6, wherein the charge transport layer has a thickness of 8–20μ.

8. The electrophotographic photosensitive member according to claim 1, wherein the charge generation layer contains at least one charge-generating material selected from the group consisting of selenium, selenium-tellurium, pyrylium dyes or co-crystalline complexes thereof, thiapyrylium dyes or co-crystalline complexes thereof, phthalocyanine pigments, anthanthrone pigments, dibenzpyrenequinone pigments, pyranthrone pigments, trisazo pigments, disazo pigments, monoazo pigments, quinacridone pigments, asymmetric or symmetric quinocyanine pigments, squaric acid methine dyes, indigo dyes, thioindigo dyes, cadmium sulfide, and amorphous silicon.

9. The electrophotographic photosensitive member according to claim 8, wherein the charge generation layer contains a disazo pigment and a binder.

10. The electrophotographic photosensitive member according to claim 8, wherein the charge generation layer contains copper phthalocyanine and a binder.

11. The electrophotographic photosensitive member according to claim 8 wherein the charge generation layer is an amorphous silicon film.

12. The electrophotographic photosensitive member according to claim 1, wherein n in the general formula (1) is zero.

13. The electrophotographic photosensitive member according to claim 1, wherein both $R_{11}$ and $R_{12}$ in the general formula (1) are alkyl groups of 1–4 carbon atoms.

14. The electrophotographic photosensitive member according to claim 13, wherein said alkyl groups are each methyl or ethyl.

15. The electrophotographic photosensitive member according to claim 1, wherein both $R_{11}$ and $R_{12}$ in the general formula (1) are phenyl groups.

16. The electrophotographic photosensitive member according to claim 1, wherein both $R_{13}$ and $R_{14}$ in the general formula (1) are alkyl groups of 1–4 carbon atoms.

17. The electrophotographic photosensitive member according to claim 16, wherein said alkyl groups are each methyl or ethyl.

18. The electrophotographic photosensitive member according to claim 1, wherein both $R_{13}$ and $R_{14}$ in the general formula (1) are alkoxy groups of 1–4 carbon atoms.

19. The electrophotographic photosensitive member according to claim 18, wherein said alkoxy groups are each methoxy or ethoxy.

20. The electrophotographic photosensitive member according to claim 1, wherein both $R_{15}$ and $R_{16}$ in the general formula (1) are aryl or aryl substituted by alkyl, alkoxy, halogen or dialkylamino groups.

21. The electrophotographic photosensitive member according to claim 1, wherein both $R_{21}$ and $R_{22}$ in the general formula (2) are alkyl groups of 1–4 carbon atoms.

22. The electrophotographic photosensitive member according to claim 21, wherein said alkyl groups are each methyl or ethyl.

23. The electrophotographic photosensitive member according to claim 1, wherein both $R_{21}$ and $R_{22}$ in the general formula (2) are phenyl groups.

24. The electrophotographic photosensitive member according to claim 1, wherein $Ar_1$ in the general formula (2) is phenylene or phenylene substituted by alkyl, alkoxy or halogen.

25. The electrophotographic photosensitive member according to claim 1, wherein $Ar_2$ in the general formula (2) is phenylene or phenylene substituted by alkyl, alkoxy or halogen.

26. An electrophotographic photosensitive member having a conductive substrate and a photosensitive layer, characterized in that the photosensitive layer comprises a binder, a charge-generating material, and at least one hydrazone compound represented by the following general formula (1) or (2):

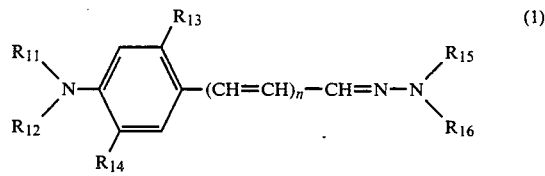

wherein $R_{11}$ and $R_{12}$ independently of each other represent alkyl, aralkyl, phenyl, alkyl substituted by alkoxy, halogen or dialkylamino, aralkyl substituted by alkyl, alkoxy, halogen or dialkylamino, phenyl substituted by alkyl, alkoxy, halogen or dialkylamino, or $R_{11}$ and $R_{12}$ form a 5- or 6-membered ring residue conjointly with the nitrogen atom to which they are bonded; $R_{13}$ and $R_{14}$ independently of each other represent alkyl or alkoxy; $R_{15}$ and $R_{16}$ independently of each other represent alkyl, aralkyl, aryl, aralkyl substituted by alkyl, alkoxy, halogen or dialkylamino, or aryl substituted by alkyl, alkoxy, halogen or dialkylamino; and n represents an integer of 0 l or 1, and

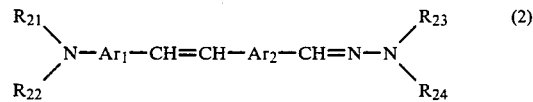

wherein $R_{21}$ and $R_{22}$ independently of each other represents alkyl, aralkyl, phenyl, alkyl substituted by alkoxy, halogen or dialkylamino, aralkyl substituted by alkyl, alkoxy, halogen or dialkylamino, or $R_{21}$ and $R_{22}$ form a 5- or 6-member ring residue conjointly with the nitrogen atom to which they are bonded; $R_{23}$ and $R_{24}$ independently of each other represent alkyl, aralkyl, aryl, alkyl substituted by alkoxy, halogen or dialkylamino, aralkyl substituted by alkyl, alkoxy, halogen or dialkylamino or aryl substituted by alkyl, aralkyl, halogen or dialkylamino; and $Ar_1$ and $Ar_2$ independently of each other represent arylene or arylene substituted by alkyl, alkoxy or halogen.

27. The electrophotographic photosensitive member according to claim 26, wherein the photosensitive layer contains a photoconductive polymer.

28. The electrophotographic photosensitive member according to claim 26, wherein the charge-generating material is at least one compound selected from the group consisting of pyrylium dyes or co-crystalline complexes thereof, thiapyrylium dyes or co-crystalline complexes thereof, phthalocyanine pigments, anthonthrone pigments, dibenzpyrenequinone pigments, pyranthrone pigments, trisazo pigments, disazo pigments, monoazo pigments, indigo pigments, quinacridone pigments, asymmetric or symmetric quinocyanine, cadmium sulfide, and squaric acid methine dyes.

29. The electrophotographic photosensitive member according to claim 28, wherein the charge-generating material is a disazo pigment.

30. The electrophotographic photosensitive member according to claim 26, wherein the binder is at least one resin selected from the group consisting of polyarylate, polysulfone, polyamide, polystyrene, acrylic resin, methacrylic resin, polyacrylonitrile resin, polyvinyl chloride resin, polyvinyl acetate resin, phenolic resin, epoxy resin, polyester resin, alkyd resin, polycarbonate, polyurethane, a copolymer of monomers constituting said resins, a copolymer of butadiene and a monomer constituting said resins, cellulose ester resin, and cellulose ether resin.

31. The electrophotographic photosensitive member according to claim 26, wherein n in the general formula (1) is zero.

32. The electrophotographic photosensitive member according to claim 26, wherein both $R_{11}$ and $R_{12}$ in the general formula (1) are alkyl groups of 1–4 carbon atoms.

33. The electrophotographic photosensitive member according to claim 32, wherein said alkyl groups are each methyl or ethyl.

34. The electrophotographic photosensitive member according to claim 26, wherein both $R_{11}$ and $R_{12}$ in the general formula (1) are phenyl groups.

35. The electrophotographic photosensitive member according to claim 26, wherein both $R_{13}$ and $R_{14}$ in the general formula (1) are alkyl groups of 1–4 carbon atoms.

36. The electrophotographic photosensitive member according to claim 35, wherein said alkyl groups are each methyl or ethyl.

37. The electrophotographic photosensitive member according to claim 26, wherein both $R_{13}$ and $R_{14}$ in the general formula (1) are alkoxy groups of 1–4 carbon atoms.

38. The electrophotographic photosensitive member according to claim 37, wherein said alkoxy groups are each methoxy or ethoxy.

39. The electrophotographic photosensitive member according to claim 26, wherein both $R_{15}$ and $R_{16}$ in the general formula (1) are aryl or aryl substituted by alkyl, alkoxy, halogen or dialkylamino groups.

40. The electrophotographic photosensitive member according to claim 26, wherein both $R_{21}$ and $R_{22}$ in the general formula (2) are alkyl groups of 1–4 carbon atoms.

41. The electrophotographic photosensitive member according to claim 40, wherein said alkyl groups are each methyl or ethyl.

42. The electrophotographic photosensitive member according to claim 26, wherein both $R_{21}$ and $R_{22}$ in the general formula (2) are phenyl groups.

43. The electrophotographic photosensitive member according to claim 26, wherein $Ar_1$ in the general formula (2) is phenylene or phenylene substituted by alkyl, alkoxy or halogen.

44. The electrophotographic photosensitive member according to claim 26, wherein $Ar_2$ in the general formula (2) is phenylene or phenylene substituted by alkyl, alkoxy or halogen.

* * * * *